US009987636B2

(12) United States Patent
Jensen et al.

(10) Patent No.: US 9,987,636 B2
(45) Date of Patent: Jun. 5, 2018

(54) METHOD AND APPARATUS FOR USE IN TEMPERATURE CONTROLLED PROCESSING OF MICROFLUIDIC SAMPLES

(71) Applicant: Caliper Life Sciences, Inc., Hopkinton, MA (US)

(72) Inventors: Morten J Jensen, San Francisco, CA (US); Andrea W Chow, Los Altos, CA (US); Colin B. Kennedy, Greenbrae, CA (US); Stephane Mouradian, Menlo Park, CA (US)

(73) Assignee: CALIPER LIFE SCIENCES, INC., Hopkinton, MA (US)

( * ) Notice: Subject to any disclaimer, the term of this patent is extended or adjusted under 35 U.S.C. 154(b) by 94 days.

(21) Appl. No.: 14/691,340

(22) Filed: Apr. 20, 2015

(65) Prior Publication Data

US 2015/0224505 A1 Aug. 13, 2015

Related U.S. Application Data

(63) Continuation of application No. 11/398,489, filed on Apr. 4, 2006, now abandoned.

(60) Provisional application No. 60/668,274, filed on Apr. 4, 2005.

(51) Int. Cl.

| | |
|---|---|
| ***C12Q 1/68*** | (2006.01) |
| ***B01L 7/00*** | (2006.01) |
| ***B01L 3/00*** | (2006.01) |

(52) U.S. Cl.

CPC ............ *B01L 7/525* (2013.01); *B01L 3/5027* (2013.01); *B01L 3/502715* (2013.01); *B01L 3/502746* (2013.01); *B01L 7/5255* (2013.01); *B01L 3/5025* (2013.01); *B01L 3/50851* (2013.01); *B01L 2300/0609* (2013.01); *B01L 2300/087* (2013.01); *B01L 2300/0816* (2013.01); *B01L 2300/0829* (2013.01); *B01L 2300/0864* (2013.01); *B01L 2300/0867* (2013.01); *B01L 2300/0877* (2013.01); *B01L 2300/1822* (2013.01); *B01L 2300/1827* (2013.01); *B01L 2400/0418* (2013.01); *B01L 2400/0487* (2013.01)

(58) Field of Classification Search

None

See application file for complete search history.

(56) References Cited

U.S. PATENT DOCUMENTS

| | | | |
|---|---|---|---|
| 4,683,202 | A | 7/1987 | Mullis |
| 4,965,188 | A | 10/1990 | Mullis et al. |
| 5,176,203 | A | 1/1993 | Larzul |
| 5,270,183 | A | 12/1993 | Corbett et al. |
| 5,460,780 | A | 10/1995 | Devaney et al. |
| 5,508,197 | A | 4/1996 | Hansen et al. |
| 5,538,848 | A | 7/1996 | Livak et al. |
| 5,587,128 | A | 12/1996 | Wilding et al. |
| 5,639,423 | A | 6/1997 | Northrup et al. |
| 5,656,493 | A | 8/1997 | Mullis et al. |
| 5,716,842 | A | 2/1998 | Baier et al. |
| 5,720,923 | A | 2/1998 | Haff et al. |
| 5,736,106 | A | 4/1998 | Ishiguro et al. |
| 5,858,195 | A | 1/1999 | Ramsey |
| 5,863,502 | A | 1/1999 | Southgate et al. |
| 5,880,071 | A | 3/1999 | Parce et al. |
| 5,885,470 | A | 3/1999 | Parce et al. |
| 5,965,001 | A | 10/1999 | Chow et al. |
| 5,994,056 | A | 11/1999 | Higuchi |
| 6,010,607 | A | 1/2000 | Ramsey |
| 6,046,056 | A | 4/2000 | Parce et al. |
| 6,210,958 | B1 * | 4/2001 | Brust ................. B01L 3/50851 165/201 |
| 6,408,878 | B2 | 6/2002 | Unger et al. |
| 6,409,900 | B1 | 6/2002 | Parce et al. |
| 6,425,972 | B1 | 7/2002 | McReynolds |

(Continued)

FOREIGN PATENT DOCUMENTS

| | | | |
|---|---|---|---|
| EP | 0504435 | A1 | 9/1992 |
| WO | 1997/036681 | A1 | 10/1997 |

(Continued)

OTHER PUBLICATIONS

Wang et al. (Droplet-based micro oscillating-flow PCR chip, J. Micromech. Microeng. 15 (2005) 1369-1377, Published May 25, 2005).*

Sun et al. (A heater-integrated transparent microchannel chip for continuous-flow PCR, Sensors and Actuators B: Chemical, vol. 84, Issues 2-3, May 15, 2002, pp. 283-289).*

Niu et al. (DNA amplification on a PDMS-glass hybrid microchip, Journal of Micromechanics and Microengineering, vol. 16, No. 2, pp. 425-433, Published Jan. 19, 2006).*

(Continued)

*Primary Examiner* — Aaron A Priest

(74) *Attorney, Agent, or Firm* — Day Pitney LLP

(57) ABSTRACT

Embodiments of the invention comprise microfluidic devices, instrumentation interfacing with those devices, processes for fabricating that device, and methods of employing that device to perform PCR amplification. Embodiments of the invention are also compatible with quantitative Polymerase Chain Reaction ("qPCR") processes. Microfluidic devices in accordance with the invention may contain a plurality of parallel processing channels. Fully independent reactions can take place in each of the plurality of parallel processing channels. The availability of independent processing channels allows a microfluidic device in accordance with the invention to be used in a number of ways. For example, separate samples could be processed in each of the independent processing channels. Alternatively, different loci on a single sample could be processed in multiple processing channels.

16 Claims, 13 Drawing Sheets

(56) References Cited

U.S. PATENT DOCUMENTS

| | | | |
|---|---|---|---|
| 6,448,066 | B1 | 9/2002 | Wheatcroft |
| 6,488,897 | B2 | 12/2002 | Dubrow et al. |
| 6,503,750 | B1 | 1/2003 | Benett et al. |
| 6,509,059 | B2 | 1/2003 | Yang et al. |
| 6,547,941 | B2 | 4/2003 | Kopf-Sill et al. |
| 6,551,839 | B2 | 4/2003 | Jovanovich et al. |
| 6,555,067 | B1 | 4/2003 | Gandhi et al. |
| 6,767,512 | B1 | 7/2004 | Lurz et al. |
| 6,787,338 | B2 | 9/2004 | Wittwer et al. |
| 6,821,771 | B2 | 11/2004 | Festoc |
| 6,841,193 | B1 | 1/2005 | Yang et al. |
| 6,849,411 | B2 | 2/2005 | Knapp et al. |
| 6,915,679 | B2 | 7/2005 | Chien et al. |
| 6,977,145 | B2 | 12/2005 | Fouillet et al. |
| 7,030,340 | B2 | 4/2006 | Knoche |
| 2002/0025280 | A1 | 2/2002 | Chazan et al. |
| 2002/0079845 | A1 | 6/2002 | Kirkpatrick et al. |
| 2003/0138829 | A1 | 7/2003 | Unger et al. |
| 2004/0115799 | A1 | 6/2004 | Gutierrez |
| 2004/0224325 | A1 | 11/2004 | Knapp et al. |
| 2005/0019213 | A1 | 1/2005 | Kechagia et al. |

FOREIGN PATENT DOCUMENTS

| | | | |
|---|---|---|---|
| WO | 2002/060584 | A2 | 8/2002 |
| WO | 2005/094981 | A1 | 10/2005 |

OTHER PUBLICATIONS

Definition of "port" at dictionary.com, accessed Feb. 6, 2014.

Wilding et al. (Clin Chem. Sep. 1994;40(9):1815-8).

USPTO's Non-Final Office Action issued in corresponding U.S. Appl. No. 11/398,489, filed Jan. 9, 2009.

USPTO's Final Office Action issued in corresponding U.S. Appl. No. 11/398,489, filed Aug. 10, 2009.

USPTO's Non-Final Office Action issued in corresponding U.S. Appl. No. 11/398,489, filed Jan. 25, 2010.

USPTO's Final Office Action issued in corresponding U.S. Appl. No. 11/398,489, filed Jul. 26, 2010.

USPTO's Non-Final Office Action issued in corresponding U.S. Appl. No. 11/398,489, filed Sep. 20, 2013.

USPTO's Final Office Action issued in corresponding U.S. Appl. No. 11/398,489, filed Mar. 11, 2014.

* cited by examiner

METHOD AND APPARATUS FOR USE IN TEMPERATURE CONTROLLED PROCESSING OF MICROFLUIDIC SAMPLES

CROSS-REFERENCE TO RELATED APPLICATIONS

This application is a continuation of U.S. patent application Ser. No. 11/398,489, filed Apr. 4, 2006, which claims the benefit of U.S. Provisional Patent Application Ser. No. 60/668,274, filed Apr. 4, 2005, each of which is hereby incorporated by reference for all purposes as if set forth herein verbatim.

BACKGROUND OF THE INVENTION

Field of the Invention

The present invention relates to microfluidic processing of biological samples and, more particularly, to methods and apparatuses for use in temperature controlled processing of biological samples in a microfluidic device.

Description of the Related Art

Microfluidics refers to a set of technologies involving the flow of fluids through channels having at least one linear interior dimension, such as depth or diameter, of less than 1 mm. It is possible to create microscopic equivalents of bench-top laboratory equipment such as beakers, pipettes, incubators, electrophoresis chambers, and analytical instruments within the channels of a microfluidic device. Since it is also possible to combine the functions of several pieces of equipment on a single microfluidic device, a single microfluidic device can perform a complete analysis that would ordinarily require the use of several pieces of laboratory equipment. A microfluidic device designed to carry out a complete chemical or biochemical analyses is commonly referred to as a micro-Total Analysis System (μ-TAS) or a "lab-on-a chip."

A lab-on-a-chip type microfluidic device, which can simply be referred to as a "chip," is typically used as a replaceable component, like a cartridge or cassette, within an instrument. The chip and the instrument form a complete microfluidic system. The instrument can be designed to interface with microfluidic devices designed to perform different assays, giving the system broad functionality. For example, the commercially available Agilent 2100 Bioanalyzer system can be configured to perform four different types of assays—DNA (deoxyribonucleic acid), RNA (ribonucleic acid), protein, and cell assays—by simply placing the appropriate type of chip into the instrument.

In a typical microfluidic system, the microfluidic channels are in the interior of the chip. The instrument interfacing with the chip performs a variety of different functions: supplying the driving forces that propel fluid through the channels in the chip, monitoring and controlling conditions (e.g., temperature) within the chip, collecting signals emanating from the chip, introducing fluids into and extracting fluids out of the chip, and possibly many others. The instruments are typically computer controlled so that they can be programmed to interface with different types of chips and to interface with a particular chip in such a way as to carry out a desired analysis.

Microfluidic devices designed to carry out complex analyses will often have complicated networks of intersecting channels. Performing the desired assay on such chips will often involve separately controlling the flows through certain channels, and selectively directing flows through channel intersections. Fluid flow through complex interconnected channel networks can be accomplished either by building microscopic pumps and valves into the chip or by applying a combination of externally-generated driving forces to the chip. Examples of microfluidic devices with pumps and valves are described in U.S. Pat. No. 6,408,878, which represents the work of Dr. Stephen Quake at the California Institute of Technology. Fluidigm Corporation of South San Francisco, Calif., is commercializing Dr. Quake's technology. The use of multiple electrical driving forces to control the flow through complicated networks of intersecting channels in a microfluidic device is described in U.S. Pat. No. 6,010,607, which represents the work Dr. J. Michael Ramsey performed while at Oak Ridge National Laboratories. The use of multiple pressure driving forces to control flow through complicated networks of intersecting channels in a microfluidic device is described in U.S. Pat. No. 6,915,679, which represents technology developed at Caliper Life Sciences, Inc. of Hopkinton, Mass.

Lab-on-a-chip type microfluidic devices offer a variety of inherent advantages over conventional laboratory processes such as reduced consumption of sample and reagents, ease of automation, large surface-to-volume ratios, and relatively fast reaction times. Thus, microfluidic devices have the potential to perform diagnostic assays more quickly, reproducibly, and at a lower cost than conventional devices. The advantages of applying microfluidic technology to diagnostic applications were recognized early on in development of microfluidics. In U.S. Pat. No. 5,587,128, Drs. Peter Wilding and Larry Kricka from the University of Pennsylvania describe a number of microfluidic systems capable of performing complex diagnostic assays. For example, Wilding and Kricka describe microfluidic systems in which the steps of sample preparation, PCR (polymerase chain reaction) amplification, and analyte detection are carried out on a single chip.

For the most part, the application of microfluidic technology to diagnostic applications has failed to reach its potential, so only a few such systems are currently on the market. Two of the major shortcomings of current microfluidic diagnostic devices relate to cost and to difficulties in sample preparation. Issues related to cost arise because materials that are inexpensive to process into chips, such as many common polymers, are not necessarily chemically inert, thermally stable, or optically transparent enough to be suitable for diagnostic applications. To address the cost issue, technology has been developed that allows microfluidic chips fabricated from more expensive materials to be reused, lowering the cost per use. See U.S. Published Application No. 2005/0019213. However, when chips are reused, issues of cross-contamination from previously processed samples could arise. The best solution may be to overcome the limitations of currently available polymer materials so that a chip can be manufactured inexpensively enough to be disposed of after a single use.

It is an object of the present invention to employ microfluidic devices for the performance of assays, such as PCR, that could be relevant to diagnostic applications. In particular, it is an object of the invention to provide methods and apparatuses based on microfluidic technology that allow PCR amplification and analyte detection to be performed in a cost-effective manner.

These and further objects will be more readily appreciated when considering the following disclosure and appended claims.

SUMMARY OF THE INVENTION

In various embodiments and aspects, the invention comprises a microfluidic device, instrumentation interfacing with that device, processes for fabricating that device, and methods of employing that device. Embodiments of the invention provide microfluidic devices capable of performing PCR amplification. Embodiments of the invention are also compatible with quantitative Polymerase Chain Reaction ("qPCR") processes.

In an illustrative embodiment, the microfluidic device contains a plurality of parallel processing channels. Fully independent reactions can take place in each of the plurality of parallel processing channels. The availability of independent processing channels allows a microfluidic device in accordance with the invention to be used in a number of ways. For example, separate samples could be processed in each of the independent processing channels. Alternatively, different loci on a single sample could be processed in multiple processing channels.

Microfluidic devices in accordance with the invention may comprise wells configured to receive the reagents to be used and the samples to be processed in the device. In order to make the microfluidic device compatible with industry standard liquid handling equipment, the wells could be arranged in the same pattern and with the same spacing as the wells on industry standard multiwell plates. For example, the wells could be arranged in the same pattern as the wells on standard 96, 384, or 1536 well microtiter plates. Some of the reagents to be used in the device could be stored in the device in dry form, so that they can be reconstituted through the addition of liquid when the processing of a sample is to take place.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Figure 1A:
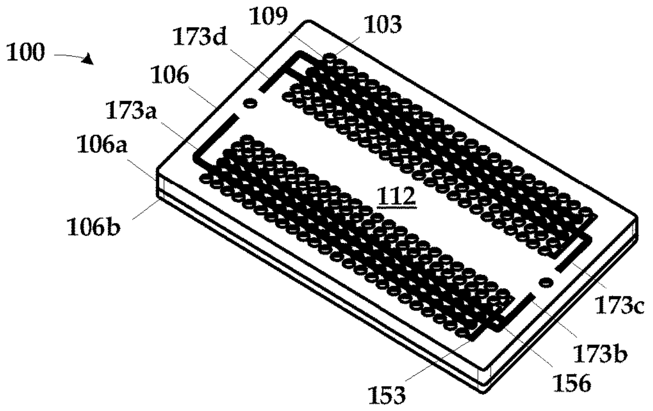
FIG. 1A-FIG. 1D depict a microfluidic device in a first embodiment in accordance with one aspect of the present invention.

FIG. 1A illustrates a microfluidic device 100 in a first embodiment in accordance with one aspect of the present invention. The device 100 comprises a plate 106 defining a plurality of wells 103 (only one indicated) for holding microfluidic samples 109 (only one indicated) or other fluids such as reagents for use in the analysis performed within the microfluidic device 100. The precise number of the wells 103 is not material to the practice of the invention. The wells 103 are arranged, or laid out, in a pattern defining a heating area 112. The geometry and location of the heating area 112 is not material to the practice of the invention other than to the extent that it impacts the design of the heating elements, discussed further below. Consequently, the layout of the wells 103 may vary in alternative embodiments.

Figure 1D:
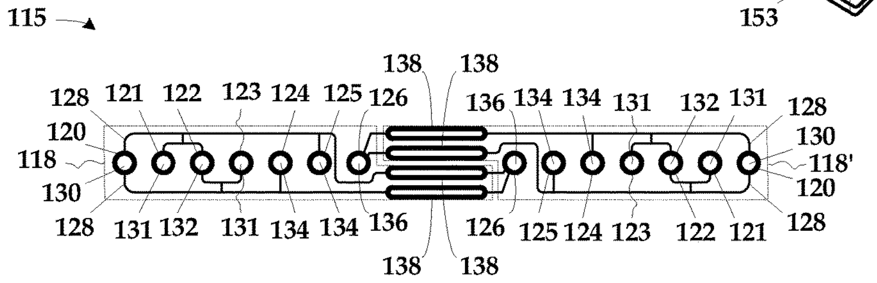
Figure 1B:
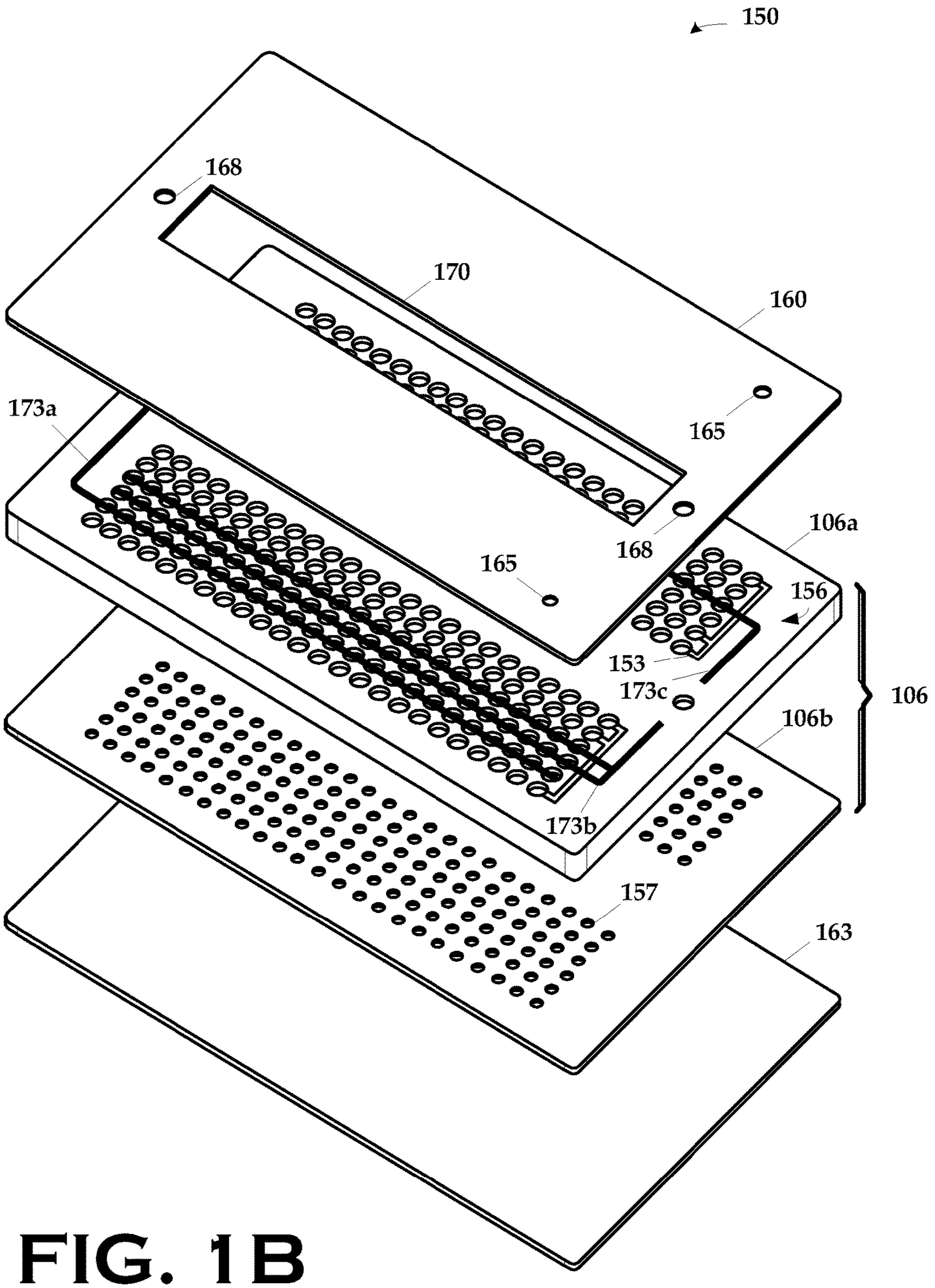

FIG. 1B provides an exploded view of the microfluidic device 100 shown in FIG. 1A. In the illustrated embodiment, the microfluidic device 100 is employed as part of an assembly 150, which also comprises first and second, or "top" and "bottom," covers 160, 163. The plate 106 comprises a caddy **106*a* and a body structure 106*b*. The caddy 106*a* includes not only the wells 103, but also a pneumatic circuit 153 and an electrical circuit 156. The pneumatic circuit 153 comprises a plurality of pneumatic surface channels (not individually indicated) in the illustrated embodiment. The electrical circuit 156 comprises embedded conductive polymer electrodes (also not individually indicated). Note that the pneumatic and electrical circuits 153, 156 may be implemented in alternative embodiments in any suitable manner known to the art. The body structure 106*b* includes the microfluidic structure of the microfluidic device 100**, i.e., the microfluidic channels and such that are described more fully below.

For present purposes, however, note that the body structure 106*b* defines a plurality of ports 157 (only one indicated) into the microfluidic circuits (not yet shown) that align with the wells 103, which are formed in the caddy 106*b*. In general, the ports 157 will be relatively small, as is the case generally with microfluidic devices such as the device 100. To ease difficulties associated with that size, the wells 103 of the caddy 106*a* are usually significantly larger. Thus, the wells 103 are loaded with fluids 109 and the fluids 109 are then loaded into the microfluidic circuits within the body structure 106*b* through these ports 157. In such an embodiment, the ports into the microfluidic circuits can be formed as "funnels", with a larger opening at the surface and a narrower opening into the microfluidic circuit. The structural interface between the caddy 106*a* and the body structure 106*b* may be, for example, the same as that disclosed in U.S. Pat. No. 6,488,897, entitled "Microfluidic Devices and Systems Incorporating Cover Layers", issued Dec. 3, 2002, to Caliper Technologies Corp. as assignee of the inventors Robert S. Dubrow, et al., although others may be used.

In the illustrated embodiment of FIG. 1A-FIG. 1D, the caddy 106*a* not only provides wells for the retention of samples and reagents, but also structurally supports and protects the body structure 106*b*. Traditionally, the body structures of microfluidic devices are constructed of glass, which can be a fragile material and caddies helped protect the body structure from damage. Certain embodiments may comprise a body structure 106*b* made of glass, and the caddy 106*a* would be used in that role in those embodiments. However, the body structure 106*a* of the illustrated embodiment is fabricated from plastic, as will be discussed further below, as is the caddy 106*a*.

The assembly 150 includes not only the microfluidic device 100, but also first and second, or "top" and "bottom," covers 160, 163. The first cover 160 includes pneumatic access ports 165 and electrical access ports 168 through which a pressure (e.g. a vacuum) and electrical power respectively may be supplied to the pneumatic and electrical circuits 153, 156. The first cover 160 also includes a cutout 170, whose function will be discussed below. As will be apparent from the discussion below, the cutout 170 may be omitted in some embodiments. Note that the terms "top" and "bottom" as used in this paragraph are defined relative to the nominal orientation of the assembly 150 in FIG. 1B.

The microfluidic device 100, first cover 160, and second cover 163 may be assembled in any manner known to the art. Note that the first cover 160 does not provide access to the individual wells 103, and is therefore assembled after the fluids 109 are deposited into the wells 103. This may affect the techniques used in assembly in some embodiments. In general, the caddy 106*a* and body structure 106*b* of the plate 106, the top cover 160, and the bottom cover 163 may be, for example, adhered or fastened together. In the illustrated embodiment, the caddy 106*a* and body structure 106*b* are laminated together, as is the bottom cover 163. The structural interface between the caddy 106*a* and the body structure 106*b* can be that as described in previously cited U.S. Pat. No. 6,488,897. In disposable embodiments, the manner in which the top cover 160 is assembled is not material, but may be taken into account in embodiments in which the microfluidic device 100 might be reused.

Figure 1C:
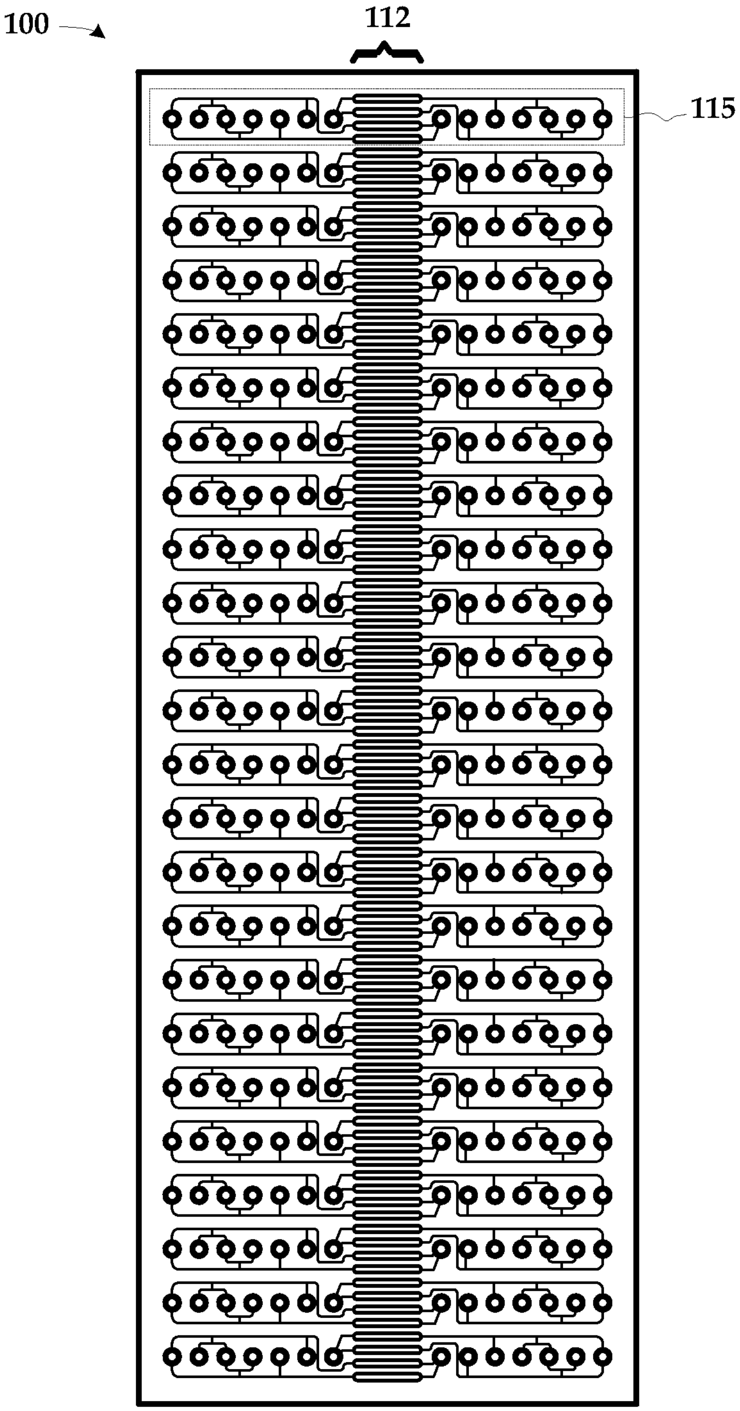

A more detailed view of the ports and channels on body structure 106*b* is shown in FIG. 1C. The invention admits wide variation in the port layout and geometry, including variations in the layout of the microfluidic channels interconnecting the ports. The microfluidic device 100 is intended, in the illustrated embodiment, for use in an analysis comprising PCR. The ports and channels on the body structure 106*b* form a plurality of separate microfluidic circuits 115 (only one indicated).

FIG. 1D, shows a close-up view of two microfluidic circuits 118, 118', one of which corresponds to circuit 115 indicated in FIG. 1C. In the embodiment shown in FIG. 1D, each of the microfluidic circuits 118, 118' comprises a plurality of ports 120-126 and microfluidic channels 128. The microfluidic channels 128 are actually fabricated in the interior of the microfluidic device 100, more particularly in the interior of body structure 106*b*, and interconnect the ports 120-126 in the manner shown. The microfluidic circuits 118, 118' also include reaction chambers 138. The enzyme 130 for the PCR is loaded in the port 120; the microfluidic sample 131 (or "lysate") is loaded in the ports 121, 123; the dried selective ion extraction ("SIE") buffer 132 is loaded in the port 122; the dried primers and probes, i.e., the locus specific reagents ("LSR"), 134 are loaded in the ports 124, 125. Waste 136 from the PCR reaction is deposited in the ports 126.

Techniques for the manufacture of microfluidic ports (e.g., the ports 120-126) and channels (e.g., the channels 128) are known to the art for embodiments in which the body structure 106*b* is fabricated from glass or plastic. These known techniques will be readily adaptable to the present invention by those in the art having the benefit of this disclosure. For embodiments in which the body structure 106*b* is fabricated from plastic, traditional manufacturing techniques employed in polymer processing may be used. For instance, body structure 106*b*, or a plurality of components that are assembled to form body structure 106*b*, may be molded and laminated, or cast and milled, or some combination of these techniques. This proposition also holds for the caddy 106*a*. Such manufacturing techniques are well known across a number of arts, and should also be readily adaptable to the present invention by those in the art having the benefit of this disclosure.

A variety of substrate materials may be employed to fabricate a microfluidic device such as device 100 in FIG. 1A-FIG. 1D. Typically, since some structures such as the grooves or trenches will have a linear dimension of less than 1 mm, it is desirable that the substrate material be compatible with known microfabrication techniques such as photolithography, wet chemical etching, laser ablation, reactive ion etching ("RIE"), air abrasion techniques, injection molding, LIGA methods, metal electroforming, or embossing. Another factor to consider when selecting a substrate material is whether the material is compatible with the full range of conditions to which the microfluidic devices may be exposed, including extremes of pH, temperature, salt concentration, and application of electric fields. Yet another factor to consider is the surface properties of the material.

Properties of the interior channel surfaces determine how these surfaces chemically interact with materials flowing through the channels, and those properties will also affect the amount of electroosmotic flow that will be generated if an electric field is applied across the length of the channel. Techniques have been developed to either chemically treat or coat the channel surfaces so that those surfaces have the desired properties. Examples of processes used to treat or coat the surfaces of microfluidic channels can be found in:

U.S. Pat. No. 5,885,470, entitled "Controlled Fluid Transport in Microfabricated Polymeric Substrates", issued Mar. 23, 1999, to Caliper Technologies Corp. as assignee of the inventors John W. Parce, et al.;

U.S. Pat. No. 6,841,193, entitled "Surface Coating for Microfluidic Devices that Incorporate a Biopolymer Resistant Moiety", issued Jan. 11, 2005, to Caliper Life Sciences, Inc. as assignee of the inventors Hua Yang, et al.;

U.S. Pat. No. 6,409,900, entitled "Controlled Fluid Transport in Microfabricated Polymeric Substrates", issued Jun. 25, 2002, to Caliper Technologies Corp. as assignee of the inventors John W. Parce, et al.; and U.S. Pat. No. 6,509,059, entitled "Surface Coating for Microfluidic Devices that Incorporate a Biopolymer Resistant Moiety", issued Jan. 21, 2003, to Caliper Technologies Corp. as assignee of the inventors Hua Yang, et al.

These patents are hereby incorporated by reference as if expressly set forth verbatim herein for their teachings regarding the treatment and/or coating of microfluidic channels. Methods of bonding two substrates together to form a completed microfluidic device are also known in the art, for example:

U.S. Pat. No. 6,425,972, entitled "Methods of Manufacturing Microfabricated Substrates", issued Jul. 30, 2002, to Caliper Technologies Corp. as assignee of the inventor Richard J. McReynolds; and U.S. Pat. No. 6,555,067, entitled "Polymeric Structures Incorporating Microscale Fluidic Elements", issued Apr. 29, 2003, to Caliper Technologies Corp. as assignee of the inventors Khushroo Ghandi, et al.

These patents are hereby incorporated by reference as if expressly set forth verbatim herein for their teachings regarding the bonding and/or joining of two layers of substrates. Other techniques are known and may be employed.

Materials normally associated with the semiconductor industry are often used as microfluidic substrates since microfabrication techniques for those materials are well established. Examples of those materials are glass, quartz, and silicon. In the case of semiconductive materials such as silicon, it will often be desirable to provide an insulating coating or layer, e.g., silicon oxide, over the substrate material, particularly in those applications where electric fields are to be applied to the device or its contents. The microfluidic devices employed in the Agilent Bioanalyzer 2100 system are fabricated from glass or quartz because of the ease of microfabricating those materials and because those materials are generally inert in relation to many biological compounds.

Microfluidic devices can also be fabricated from polymeric materials such as polymethylmethacrylate ("PMMA"), polycarbonate, polytetrafluoroethylene (e.g., TEFLON™), polyvinylchloride ("PVC"), polydimethylsiloxane ("PDMS"), polysulfone, polystyrene, polymethylpentene, polypropylene, polyethylene, polyvinylidine fluoride, acrylonitrile-butadiene-styrene copolymer ("ABS"), cyclic-olefin polymer ("COP"), and cyclic-olefin copolymer ("COC"). Such polymeric substrate materials are compatible with a number of the microfabrication techniques described above. Since microfluidic devices fabricated from polymeric substrates can be manufactured using low-cost, high-volume processes such as injection molding, polymer microfluidic devices could potentially be less expensive to manufacture than devices made using semiconductor fabrication technology. Nevertheless, there are some difficulties associated with the use of polymeric materials for microfluidic devices. For example, the surfaces of some polymers interact with biological materials, and some polymer materials are not completely transparent to the wavelengths of light used to excite or detect the fluorescent labels commonly used to monitor biochemical systems. So even though microfluidic devices may be fabricated from a variety of materials, there are tradeoffs associated with each material choice.

Similarly, techniques for preparing and loading microfluidic samples and other fluids are also well known to the art and readily adaptable. Any suitable technique known to the art for these tasks may be employed. For instance, sample preparation and loading can be performed manually, as it has been in the past. Alternatively, sample preparation and loading may be automated, since the illustrated embodiment is designed to meet standards employed in automated processing of microtiter plates. In other words, the wells 103 are arranged in the same manner as the wells on standard format microtiter plates. That allows industry standard fluid handling equipment to be use to add and remove fluids from the wells 103. Note that there is one manner in which the illustrated embodiment departs from those standards. In a standard microtiter plate, the area corresponding to the heating area 112 would be occupied by wells. In other words, while a standard microtiter plate comprises a full rectangular array of wells, a microfluidic device in accordance with the invention will be missing the wells in the array that would occupy heating region 112. Thus, the microfluidic device 100 will have fewer wells 103 than would a microtiter plate meeting the same standard and some accommodation for this departure will be made in automated handling systems.

Figure 2A:
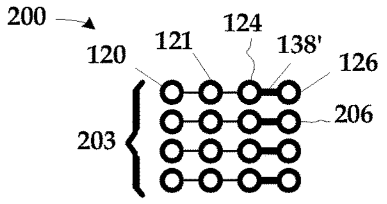
FIG. 2A-FIG. 2D show alternative well arrangements for embodiments of the microfluidic device alternative to that illustrated in FIG. 1A-FIG. 1D.
Figure 2B:
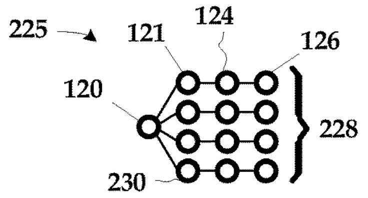
Figure 2C:
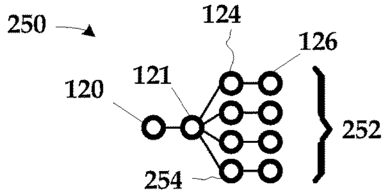
Figure 2D:
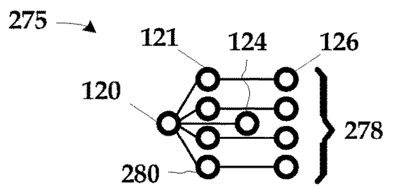

The invention admits variation in the configuration of the microfluidic circuits in various alternative embodiments of the present invention. FIG. 2A-FIG. 2D illustrate several of these alternative embodiments. FIG. 2A-FIG. 2D schematically illustrate various methods of connecting ports 120-125 to reaction chambers 138 in fluid circuits such as 118 and 118'. Note that in FIG. 1D, the channels 128 in one fluid circuit, e.g fluid circuit 118, connected to four parallel channels that form reaction chambers 138, and then the fluid path from those four channels 138 lead into port 126. In the interconnection arrangement shown in FIG. 2A, each reaction chamber 138 is connected to a separate set of ports (one set is designated 120,121,124), each set of ports being connected by a single channel. To carry out PCR in each reaction chamber 138, the first port 120 could contain the enzymes and dNTPs, the second port 121 could contain a DNA sample, and the third port could contain the probes and primers required to amplify that sample. If a flow of fluid is established out of port 120 through ports 121 and 124, the fluid entering reaction chamber 138 would contain all of the reagents required to PCR amplify the DNA in the sample. Flow could then be stopped, and reaction chamber 138 could be subjected to the sequence of temperatures required to carry out PCR amplification. After amplification is complete, flow through the fluid circuit would be reinitiated so the amplified product could flow into reservoir 126. In the embodiment in FIG. 2A, each of the four reaction chambers could be supplied with a different DNA sample, and each sample could be supplied with different probes and primers, so four completely different DNA amplifications could be carried out in parallel. FIG. 2B shows an alternative port layout. In the arrangement in FIG. 2B, common reagents, such enzymes and dNTPs could be placed in port 120, which is connected to the four separate flow paths leading into the four reaction chambers 138. Four separate DNA samples, and four separate sets of probes and primers could be placed in ports 121 and 124. PCR amplification could then be carried out in the same manner as described with respect to FIG. 2A. FIG. 2C illustrates a third embodiment in which the four reaction chambers are fed with the same enzymes and dNTPs from reservoir 120 and the same sample from reservoir 121. The four distinct reservoirs 124 could contain probes and primers for different loci, so four different portions of the sample can be amplified in the four reaction chambers 138. FIG. 2D illustrates an embodiment in which the same probes and primers flow out of port 124 into all four reaction chambers 138, the same enzymes and dNTPs flow out of port 120 into all four chambers, but different DNA samples flow into each of the four chambers 138 from the four ports 121. Other variations not shown are also possible.

Figure 3A:
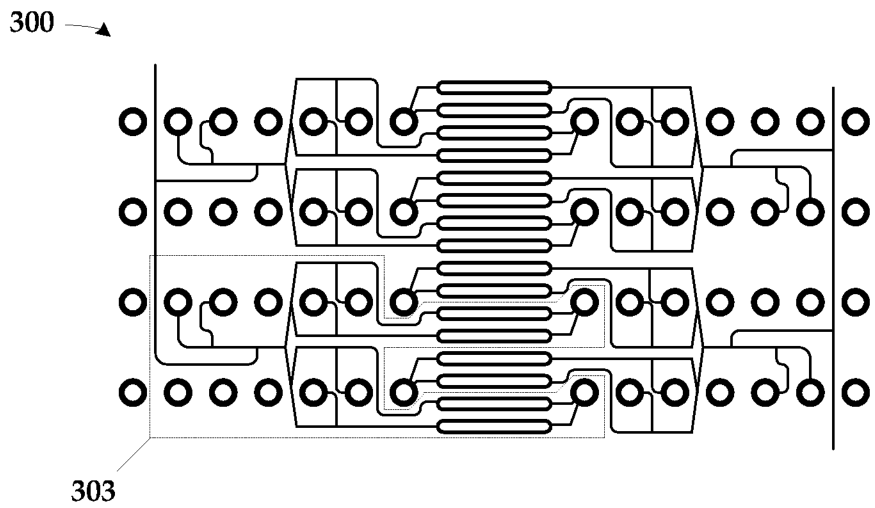
FIG. 3A-FIG. 3C show alternative microfluidic circuits that may be implemented with the port layout of FIG. 1A-FIG. 1D.
Figure 3B:
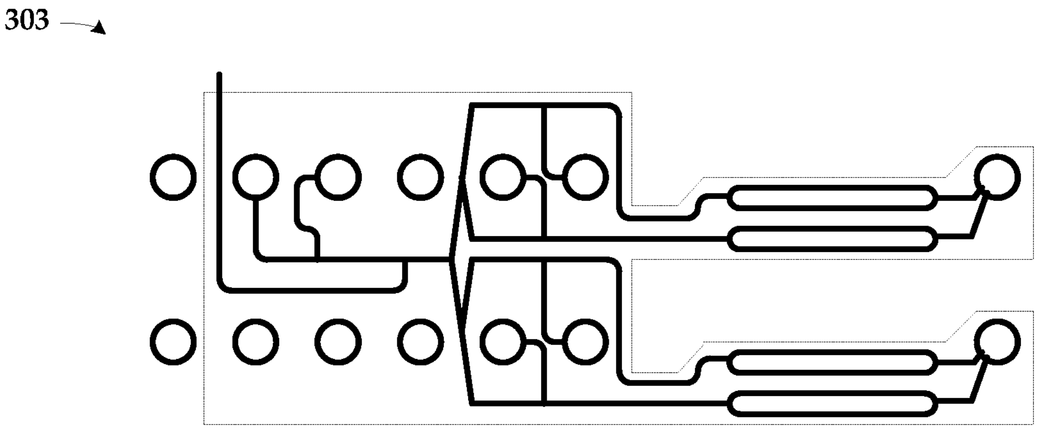
Figure 3C:
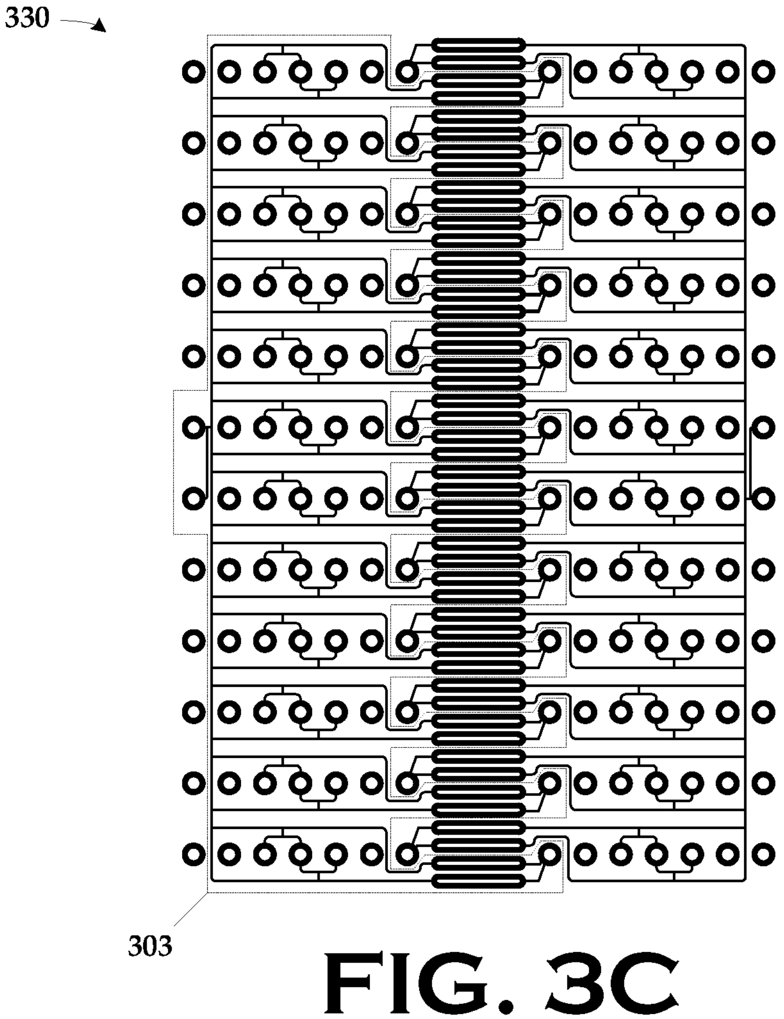

FIG. 3A-FIG. 3C illustrate how a single port layout, e.g., the port layout of the microfluidic device 100, shown in FIG. 1A-FIG. 1D, can be used to implement different microfluidic circuits. The port layout of the microfluidic device 100 includes 96 microfluidic circuits in which 96 reactions are performed, each with a single sample in a single location—e.g., a reaction reservoir 138. FIG. 3A-FIG. 3B show an embodiment 300 in which the port layout implements a plurality of microfluidic circuits 303, each of which provides four reactions from a single sample in four locations. Thus, the microfluidic device (not shown) would provide 96 reactions over 96 locations for 24 samples, each sample being reacted four times in four locations. FIG. 3C illustrates an embodiment 330 in which an microfluidic circuit 303 provides 24 samples, each reacting in one location such that four microfluidic circuits 303 will yield 96 reactions.

Returning to FIG. 1A-FIG. 1B, in accordance with one aspect of the present invention, the electrical circuit 156 comprises electrodes 173*a*-173*d* constructed of an electrically conductive polymer. In general, the polymer may be any polymer having sufficient electrical conductivity. For the illustrated embodiment, "sufficient" electrical conductivity is approximately 250 Ω/cm. Note that this also implies that the material from which the caddy 106*a* is constructed from a material that is not electrically conductive, or is an electrical insulator.

In this particular embodiment, the electrical circuit 156 is shown on the surface of the caddy 106*a*, but this is not necessary to the practice of this aspect of the invention. The electrodes 173*a*-173*d* may be at any layer of the microfluidic device 100. (Similarly, the pneumatic circuit 153 need not be fabricated on the surface in all embodiments.) Some embodiments may also find if desirable to employ separate electrodes to each well 103 rather than the four shown.

The electrodes 173*a*-173*d* may be fabricated using any suitable technique. Exemplary techniques include co-injection molding, insert molding, printing, or some form of flow of material followed by some sort of curing or hardening, or by lowering heat. However, other techniques may be employed.

Some alternative embodiments may fabricate the electrodes 173*a*-173*d* using a low melt point metal, a low melt point metal alloy, a stamped metal, a conductive ink, or a conductive gel. Still other alternative embodiments may employ still other materials. Note that fabrication techniques in these alternative embodiments will vary depending on the material from which the electrodes 173*a*-173*d* are fabricated.

Figure 4A:
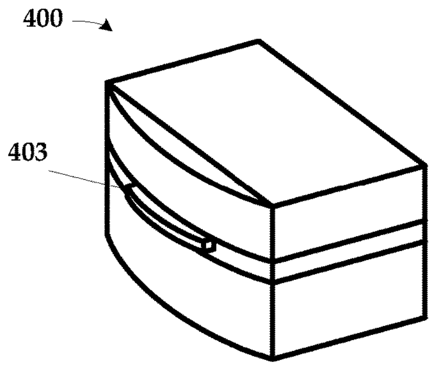
FIG. 4A-FIG. 4B depict an instrument for use in automatically processing a microfluidic device such as the microfluidic device of FIG. 1A.
Figure 4B:
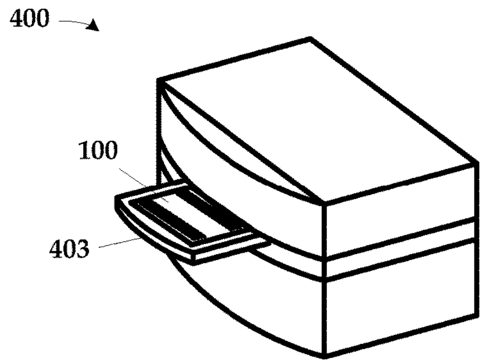

The microfluidic device 100, shown in FIG. 1A-FIG. 1D, is designed for automated processing in an instrument 400, shown in FIG. 4A-FIG. 4B. As is shown in FIG. 4B, the microfluidic device 100 is placed into a tray 403 that extends from and retracts into the instrument 400. The extension and retraction of the tray 403 may be manual. However, high precision in positioning the device 100 in the instrument 400 is desirable. Accordingly, most embodiments can use pressure sensitive servo-motor drive systems (not shown) such as are used in consumer electronics products like digital video disk ("DVD") and compact disc ("CD") players. Such drive systems have additional benefits in the illustrated embodiment as will be discussed further below.

Figure 5A:
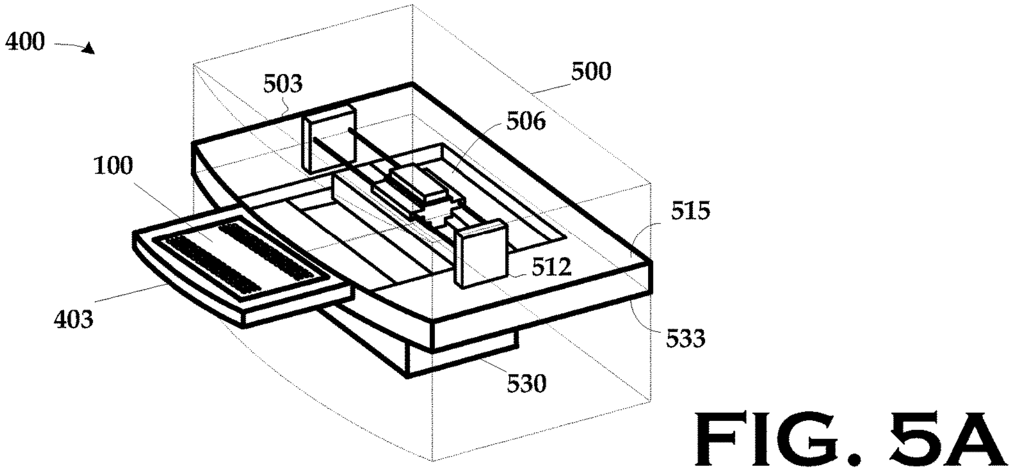
FIG. 5A-FIG. 5C depict selected aspects of the internal workings of the instrument of FIG. 4A-FIG. 4B.
Figure 5B:
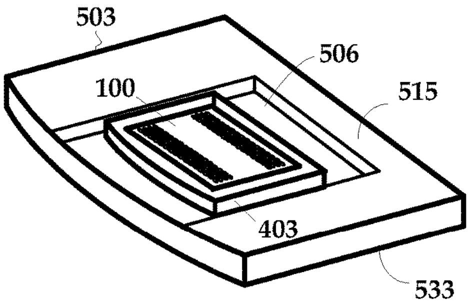
Figure 5C:
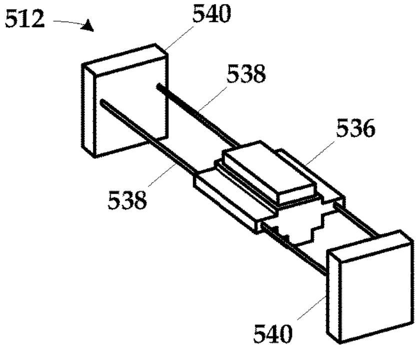

FIG. 5A-FIG. 5C illustrate selected aspects of the internal workings of the instrument 400. Accordingly, the housing 500 of the instrument is shown in ghosted lines. The drawings show the tray 403 holding the microfluidic device 100 in an extended position (in FIG. 5A) and a retracted position (in FIG. 5B). The instrument 400 includes a landing 503 that defines a bay 506 into which the tray 403 is retracted. The tray 403 is retracted into and positioned in the bay 506 for loading, processing, and evaluation as described below.

The instrument 400 also includes an optical assembly 512 mounted to the top 515 of the landing 503. The optical assembly 512 is best shown in FIG. 5C. An optical head 536 reciprocates on a pair of rails 538 between two bases 540. The optical head 536 is driven on the rails 538 by any suitable mechanism known to the art, e.g., a stepper motor (not shown). The optical assembly 512 is an optional feature for use in the optional fluorescent monitoring technique discussed more fully below in connection with FIG. 13A-FIG. 13B. Since the fluorescent monitoring technique is optional, it may be omitted in some alternative embodiments and, accordingly, so may the optical assembly 512.

Microfluidic devices such as the microfluidic device 100 may be used in a variety of applications, including, e.g., the performance of high throughput screening assays in drug discovery, immunoassays, diagnostics, genetic analysis, and the like. The wells 103 and the ports 157, shown in FIG. 1A, may be loaded through parallel or serial introduction and analysis of multiple samples. Alternatively, these devices may be coupled to a sample introduction port, e.g., a pipettor, which serially introduces multiple samples into the device for analysis. Examples of such sample introduction systems are described in, for example:

- U.S. Pat. No. 5,880,071, entitled "Electropipettor and Compensation Means for Electrophoretic Bias", issued Mar. 9, 1999, to Caliper Technologies Corporation as assignee of the inventors J. Wallace Parce et al.; and
- U.S. Pat. No. 6,046,056, entitled "High Throughput Screening Assay Systems in Microscale Fluidic Devices", issued Apr. 4, 2000, to Caliper Technologies Corporation as assignee of the inventors J. Wallace Parce et al.

These patents are hereby incorporated by reference as if expressly set forth verbatim herein for their teachings regarding automated well/port loading.

Returning to FIG. 4, the instrument 400 may, in some embodiments, furthermore include a head (not shown) with an interface by which the individual wells 103 of the microfluidic device 100 may be robotically loaded. Such a head may also be rail-mounted, and even on the rails 538. For instance, the optical head 536 can be stored at one extreme end of the rails 538 and a sample head at the other extreme end when not in use so as not to interfere with the operation of each other. The head could also carry, as a part of the interface, one or more structures through which a electrokinetic force, such as that discussed further below, may be imparted to the microfluidic circuits 118, 188'. For instance, the head could also carry structures to interface with the pneumatic circuit 153 and the electrical circuit 156 through the pneumatic access ports 165 and electrical access ports 168. Alternatively, these functions can be performed manually.

The instrument 400 further includes a thermocycler 530, constructed and operated in accordance with another aspect of the present invention, mounted to the underside 533 of the landing 503. In general, the thermocycler 530 operates by contacting the heating area 112 of the microfluidic device 100 with a series of thermal elements for a predetermined time to bring the temperature of the microfluidic samples 106 to some desired temperature and hold it there. The invention admits some variation in the manner in which this may be achieved. FIG. 6A-FIG. 6C, FIG. 7A-FIG. 7B, and FIG. 8 illustrate three alternative embodiments for accomplishing this.

Figure 6A:
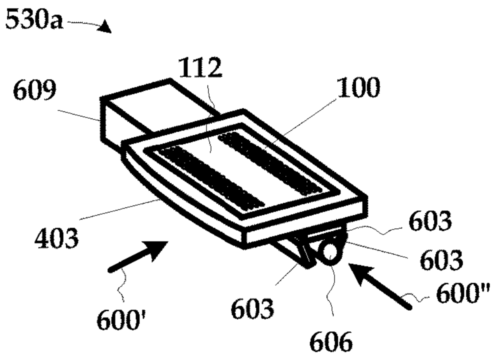
FIG. 6A-FIG. 6C, FIG. 7A-FIG. 7B, and FIG. 8 conceptually illustrate three alternative thermocyclers as may be employed in the instrument such as the instrument of FIG. 4A-FIG. 4B.
Figure 6C:
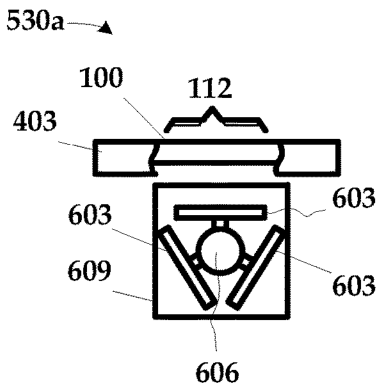
Figure 6B:
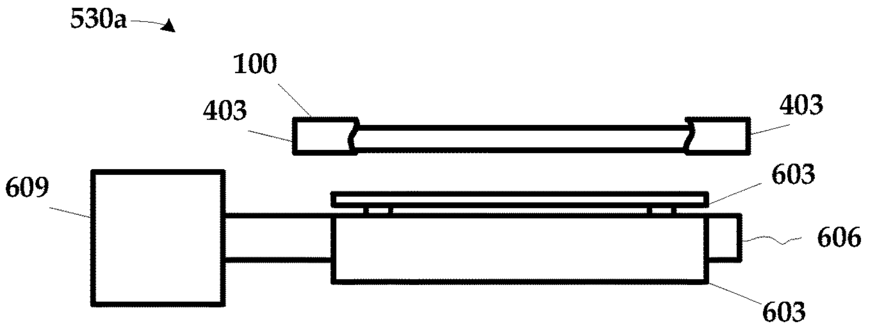

Turning now to FIG. 6A-FIG. 6C, a thermocycler 530*a* is shown. FIG. 6B is a plan, side view and FIG. 6C is a plan, end view from the direction of the arrows 600', 600", respectively, in FIG. 6A. In each of FIG. 6B and FIG. 6C, the tray 403 is shown sectioned to show the microfluidic device 100 in part. In this particular embodiment, the thermocycler 530*a* includes a plurality of temperature controlled thermal elements, i.e., three bars 603, in the illustrated embodiment. Note that the number of bars 603 is not material to the present invention. However, the number will be implementation specific depending on the number of temperatures to which the microfluidic sample 106 will be subjected during the processing. The thermocycler 530*a* also includes means for positioning a microfluidic device 100 and each of the bars 603 relative to one another in succession, i.e., a shaft 606 rotated by a drive 609 to which the bars 603 are mounted.

Note that the bars 603 are not shown contacting the microfluidic device 100, but that such contact will be found in operation. One way to initiate such contact would be to lift the shaft 606, and thus the bars 603, using the drive 609. Alternatively, a lift (not shown) may be provided for the subassembly of the drive 609, shaft 606, and bars 603. The bars 603 may be mounted to the shaft 606 using any technique known to the art provided it suffices to overcome the forces imparted by rotation of the shaft 606. The magnitude of those forces will be a function of, for instance, the speed of the rotation.

Figure 7A:
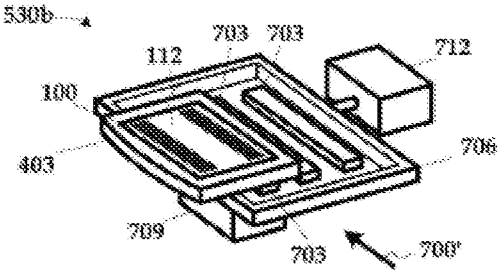
Figure 7B:
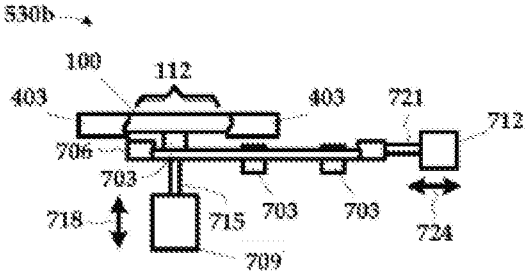

FIG. 7A-FIG. 7B illustrate a second thermocycler 530*b* as may be used in the instrument 400 of FIG. 4A-FIG. 4B. FIG. 7B is a plan, end view from the direction of the arrow 700' in FIG. 7A. In FIG. 7B, the tray 403 is shown sectioned to show the microfluidic device 100 in part. In this particular embodiment, the thermocycler 530*b* includes a plurality of temperature controlled thermal elements, i.e., three bars 703, in the illustrated embodiment. The thermocycler 530*b* also includes means for positioning a microfluidic device 100 and each of the bars 703 relative to one another in succession, i.e., a laterally sliding tray 706 in which the bars 703 are mounted; a lift 709 capable of lifting the bars 703 (with or without the tray 706) to contact the microfluidic device 100 with the bars 703; and at least one drive 712 for the tray 706 and the lift 709. In the illustrated embodiment, the lift 709 includes a dedicated drive (not shown).

More particularly, the bars 703 are placed securely in the tray 706. The lift 709 includes a shaft 715 that reciprocates, as indicated by the arrow 718. The shaft 715 operates either directly on the bars 703 extending through the tray 706, as shown in FIG. 7B, or on the bars 703 through apertures (not shown) in the tray 706. The drive 712 powers a shaft 721 that also reciprocates, as represented by the arrow 724, to translate the tray 706 laterally. Thus, in operation, the lift 709 lowers the shaft 715 to allow the bar 703 contacting the microfluidic device 100 to fall and break the contact. The drive 712 then reciprocates the shaft 721 to position the tray so that the next bar 703 is positioned between the shaft 715 and the heating area 112 of the microfluidic device 100. The lift 709 then drives the shaft 715 upward to contact the bar 703 with the microfluidic device 100. The thermocycler 530*b* iterates these acts until the process is through.

Figure 8:
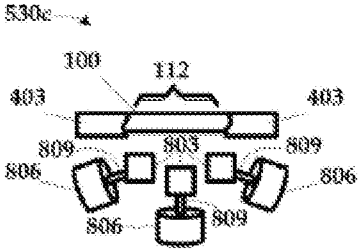

FIG. 8 illustrates a third thermocycler 530*c* as may be used in the instrument 400 of FIG. 4A-FIG. 4B in a plan, end view. Again, the tray 403 is shown sectioned to show the microfluidic device 100 in part. In this particular embodiment, the thermocycler 530*c* includes a plurality of temperature controlled thermal elements, i.e., three thermal masses 803, in the illustrated embodiment. The thermocycler 530*c* also includes means for positioning a microfluidic device 100 and each of the thermal masses 803 relative to one another in succession, i.e., a plurality of linear actuators 806, each lifting and translating a respective thermal mass 803 through a respective shaft 809 to contact the microfluidic device 100.

Figure 9:
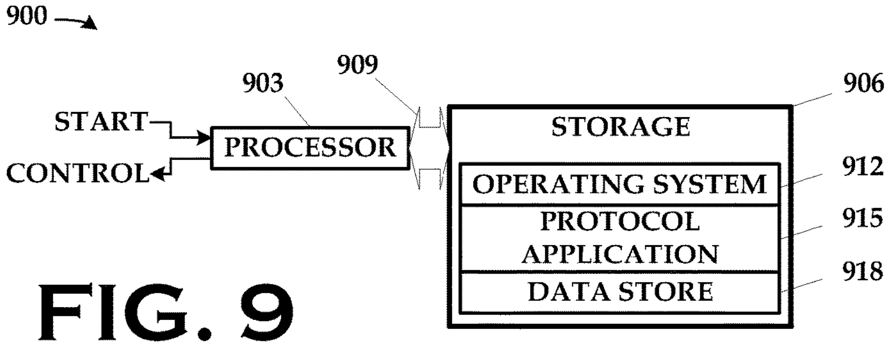
FIG. 9 illustrates one particular embodiment of a controller for use in an instrument such as the instrument of FIG. 4A-FIG. 4B.

Each of the thermocycler embodiments 530 disclosed above operate under the aegis of a controller that controls the positioning of the microfluidic device 100 and thermal elements relative to one another, and the temperatures of the thermal elements. FIG. 9 illustrates one suitable controller 900. The controller 900 is an electronic controller, although this is not necessary to the practice of the invention. In general, the controller 900 comprises a processor 903, e.g., an 8-bit microprocessor or micro-controller, communicating with a storage 906 over a bus system 909. The storage 906 may be implemented using any of a variety of technologies, such as a read-only memory ("ROM"), an electrically programmable read-only memory ("EPROM"), an erasable electrically programmable read-only memory ("EEPROM"). The storage 906 includes software residing thereon, such as an operating system ("OS") 912 and a protocol application 915.

On power-on or reset, the processor 903, under the control of the OS 912, performs a self-test and then invokes the protocol application 915. Under the direction of the protocol application, the processor 903 implements the testing protocol of the process to which the microfluidic sample 109, shown in FIG. 1A, is to be subjected. In the illustrated embodiment, the instrument 400, shown in FIG. 4, is loaded with the microfluidic device 100 containing the microfluidic sample 109, as is shown in FIG. 5A, FIG. 5B. The instrument 400 may be loaded by a technician or a robotic materials handling tool, neither of which is shown. When the instrument 400 is loaded, a START signal, shown in FIG. 9, is transmitted to the processor 903. For instance, a technician may press a "start" button (not shown) on the console (not shown) of the instrument 400 to indicate that the instrument 400 is loaded and ready for the processing to start.

Upon receiving the START signal, the processor 903 begins executing the protocol application 915. In general, on execution, the protocol application performs a method comprising cycling a microfluidic sample 109 through a plurality of thermal cycles. Each thermal cycle includes contacting a predetermined portion, i.e., the heating area 112, of a microfluidic device 100 holding the microfluidic sample 109 with a respective thermal element. The microfluidic sample 109 is then heated to a predetermined temperature for a predetermined period of time. The temperature and time data may be either hard-coded into the protocol application 915; or, retrieved by the protocol application 915 from, e.g., a data store 918; or, entered through a console.

To implement the protocol, the processor 903, in executing the protocol application, generates and transmits CON- TROL signals to the various components of the instrument 400. The content of the CONTROL signals will be implementation specific. For instance, in embodiments employing the thermocycler 530*a* of FIG. 6A-FIG. 6C, the CONTROL signals will include signals to the drive 609 to rotate the shaft 606 at the appropriate times. On the other hand, in embodiments employing the thermocycler 530*b* of FIG. 7A-FIG. 7B, the CONTROL signals will includes signals controlling the reciprocation of the shafts 715, 721 by the drives 712. These kinds of adaptations in implementation will be readily apparent and within the ability of those ordinarily skilled in the art having the benefit of this disclosure.

Figure 10:
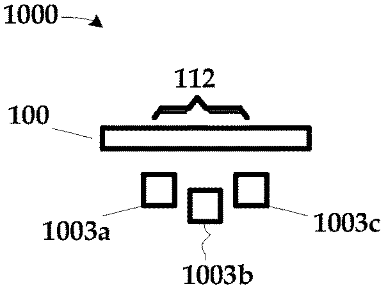
FIG. 10 illustrates the operation of the present invention in the processing protocol in one particular embodiment.

Turning now to FIG. 10, the operation 1000 of the present invention in the processing protocol in one particular embodiment will be disclosed. FIG. 10 shows a representative microfluidic device 100 including a heating area 112 and three thermal elements 1003*a*-1003*c*. Those in the art will appreciate that the microfluidic device 100 may, and typically will, hold more than a single microfluidic sample 109. The method may be applied simultaneously to each of the microfluidic samples 109 held in the microfluidic device 100. Similarly, the invention may be extended to applications in which multiple microfluidic devices 100 are processed simultaneously. Note also that FIG. 10 shows the microfluidic device 100 being heated from below, but that alternative embodiments may just as easily heat the microfluidic device 100 from above.

The illustrated embodiment is intended for use in performing a polymerase chain reaction ("PCR"). PCR is a common technique that is well known and well understood in the art. Although temperatures and durations may vary, PCR usually involves three thermal cycles—hence, the use of three thermal elements 1003*a*-1003*c*. Thus, in this particular embodiment, the microfluidic sample 109 comprises a solution of a target DNA sequence, a plurality of PCR primers, a polymerase, and a plurality of nucleotides, none of which are shown.

The process, according to the protocol implemented by the protocol application 915, shown in FIG. 9, the heats the microfluidic sample 109 denature the microfluidic sample 109. Typically, this involves heating the microfluidic sample 109 to a denaturing temperature of 95° C. for 3-10 seconds, and approximately 10 seconds in the illustrated embodiment. The process then changes the temperature of the microfluidic sample 109 to an annealing temperature of 55° C. for 3-10 seconds, and approximately 10 seconds in the illustrated embodiment. The process then changes the temperature of the microfluidic sample 109 to an elongation temperature of 72° C. for 5-30 seconds, and approximately 30 seconds in the illustrated embodiment. This process is usually iterated for 25 to 50 cycles in order to get a final product. Typically this whole process is started by heating the microfluidic sample 109 to a hot-start temperature of 95° C. for 10 minutes in order to activate the enzymes. Note, however, that other PCR protocols are known and may be implemented by the present invention.

Figure 11:
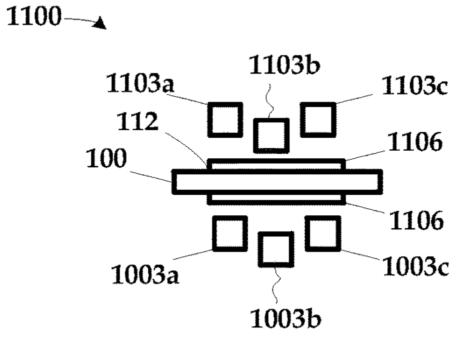
FIG. 11 illustrates the operation of the present invention in the processing protocol in a second particular embodiment.

However, the invention admits variation to help improve operational efficiency. Consider the embodiment 1100, in FIG. 11. This particular embodiment includes two optional features to improve efficiency of the apparatus. First, this particular embodiment employs a second set of thermal elements 1103*a*-1103*c* to heat the top of the microfluidic device 100. The thermal elements 1003*a*-1003*c*, 1103*a*-1103*c* apply the same temperature at the same time from both sides of the microfluidic device 100 to lower the thermal transit time. The embodiment 1100 in FIG. 11 also includes an interface material 1106 is interposed between the thermal elements 1003*a*-1003*c*, 1103*a*-1103*c* and the microfluidic device 100 at least over the heating area 112. The interface material 1106 helps eliminate poorly thermally conducting air gaps and may be some kind of phase change material, e.g., a wax that melts at the lower of the working temperatures or compliant polymers or materials like the Berquist Sil-Pad® thermally conductive insulator type of materials. The thermal interface material 1106 could also be attached to the thermal elements 1003*a*-1003*c*, 1103*a*-1103*c*. Note that these variations may be employed separately or, as in the illustrated embodiment, together.

Some embodiments may also provide fewer thermal elements 1003*a*-1003*c* than there are thermal cycles in the protocol. In the embodiments set forth illustrated herein, the implemented protocols call for a different temperature in each thermal cycle. However, some protocols may have multiple thermal cycles at the same temperature. In these embodiments, a single thermal element may be used in each thermal cycle calling for a particular temperature. It is there possible that the number of thermal elements may differ from the number of thermal cycles in some embodiments.

Figure 12A:
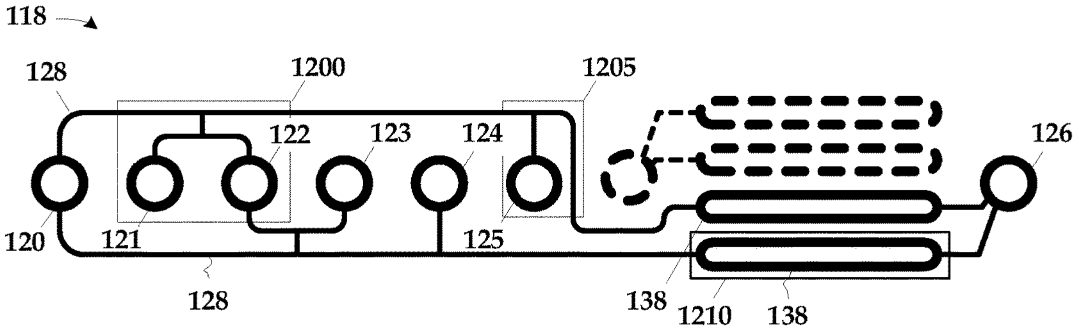
FIG. 12A-FIG. 12D illustrate a PCR reaction in the microfluidic device of FIG. 1A-FIG. 1D employing the thermocycler of FIG. 6A-FIG. 6C operated as illustrated in FIG. 10.
Figure 12B:
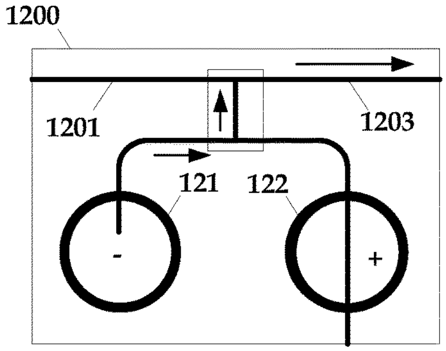
Figure 12C:
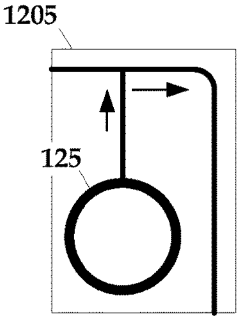
Figure 12D:
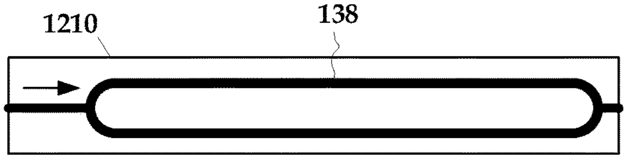

Microfluidic devices typically allow for increased automation of standard laboratory processes. This is why microfluidic devices are often referred to as "labs on a chip." Thus performing PCR in a microfluidic device allows multiple steps of the work flow associated with the PCR process to be performed on a single microfluidic device. FIG. 12A-FIG. 12D illustrate a PCR reaction in the microfluidic device of FIG. 1A-FIG. 1D employing the thermocycler of FIG. 6A-FIG. 6C operated as illustrated in FIG. 10. FIG. 12A illustrates a single microfluidic circuit 118.

As mentioned above, the enzyme 130 for the PCR is loaded in the well 120; the microfluidic sample 131 (or "lysate") is loaded in the wells 121, 123; the dried SIE buffer 132 is loaded in the well 122; the LSR 134 are loaded in the wells 124, 125. Waste from the PCR reaction is deposited in the wells 126. If the SIE buffer 132 and the locus specific reagents 134 are dried in wells 122, 124 and 125 respectively, then they are reconstituted and the electrical and pneumatic circuits 153, 156 are activated. The nucleic acid extraction occurs in a portion 1200, shown better in FIG. 12B, of the microfluidic circuit 118. The sample 103, by now reconstituted with the enzyme 130 and the buffer 132, migrates electrokinetically through the microfluidic channels 1201-1203. As the migration progresses, the extracted nucleic acid (not show) exits the portion 1200 through the channel 1203 in the direction shown. The extracted nucleic acid mixes with the LSR 134 in the portion 1205, best shown in FIG. 12C, and enters the reaction reservoir 138, where it is subjected to the thermal cycling described above and the PCR occurs. Here the reaction reservoir is shown as two parallel channels, but it may as well be 1 or more channels or containment areas.

The electrokinetic principles employed by the invention are by now known in the art. Such principles are taught, for instance, in:

U.S. Pat. No. 6,488,897, entitled "Microfluidic Devices and Systems Incorporating Cover Layers", issued Dec. 3, 2002, to Caliper Technologies Corp. as assignee of the inventors Robert S. Dubrow, et al.;

U.S. Pat. No. 5,965,001, entitled "Variable Control of Electroosmotic and/or Electrophoretic Forces Within a Fluid-Containing Structure via Electrical Forces", issued Oct. 12, 1999, to Caliper Technologies Corporation as assignee of the inventors Calvin Y. H. Chow and J. Wallace Parce, U.S. Pat. No. 6,849,411, entitled "Microfluidic Sequencing Methods", issued Feb. 1, 2005, to Caliper Life Sciences, Inc. as assignee of the inventors Michael Knapp, et al.; and U.S. Pat. No. 5,858,195, entitled "Apparatus and Method for Performing Microfluidic Manipulations for Chemical Analysis and Synthesis", issued Jan. 12, 1999, to Lockheed Martin Energy Research Corporation as assignee of the inventor J. Michael Ramsey.

These patents are hereby incorporated by reference as if expressly set forth verbatim herein for their teachings regarding electrokinetic transport. Other techniques are known and may be employed.

Figure 13A:
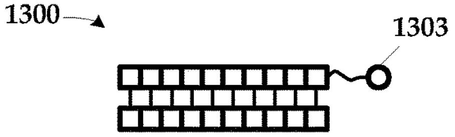
FIG. 13A-FIG. 13B depict a fluorescent monitoring as may be employed in some embodiments such as those embodiments using the instrument of FIG. 4A-FIG. 4B.

The invention also admits variation to accommodate modification and differences in protocols. For instance, DNA-based procedures like PCR routinely monitor the various aspects of the process by tagging elements of the solution with a fluorescent tag. FIG. 13A conceptually illustrates a DNA sequence 1300 tagged with a fluorescent marker 1303 in accordance with conventional practice. Thus, the present invention can implement a protocol wherein thermal cycles are interrupted, the thermal elements are removed, and the microfluidic solution 109 is fluorescently monitored with one or more wavelengths. Any suitable fluorescent monitoring technique known to the art may be used.

Figure 13B:
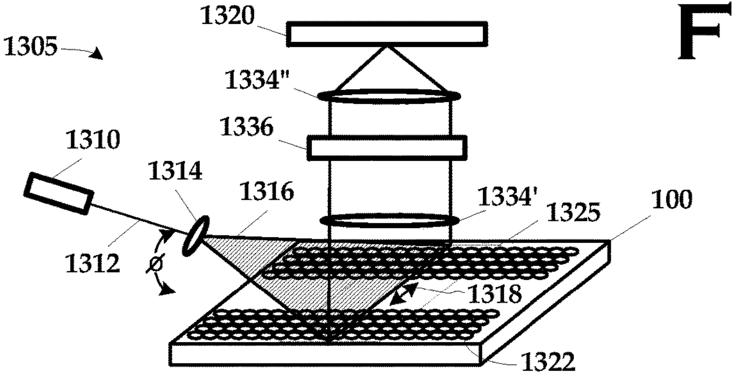

FIG. 13B conceptually illustrates one such fluorescent monitoring technique. This technique is more fully disclosed in U.S. Pat. No. 6,547,941, entitled "Ultra High Throughput Microfluidic Analytical Systems and Methods", on Apr. 15, 2003, to Caliper Technologies Corp., as assignee of the inventors Anne R. Kopf-Sill et al. This patent is hereby incorporated by reference as if set forth verbatim herein for its teachings regarding the fluorescent monitoring techniques. A portion of that disclosure will now be excerpted with slight modification relevant to its use with the present invention.

More particularly, FIG. 13B illustrates an illumination and detection system 1305 according to this particular embodiment of the present invention. The illumination and detection system 1305 includes an excitation source 1310 and a detector array 1320 including one or more optical detectors, such as CCD arrays. The excitation source 1310 provides an excitation beam 1312, which is optically focused and controlled by one or more optical elements 1314 (only one shown). In a preferred embodiment, the optical elements 1314 include one or more lenses, such as plano-convex lenses and plano-cylindrical lenses, that focus the excitation beam 1312 into a large aspect ratio elliptical illumination beam 1316 as shown.

The optical elements 1314 are positioned and arranged such that the elliptical spot 1316 is focused to the detection region 1325 on the sample microfluidic device 100. Preferably, the source 1310 and/or optical elements 1314 are positioned such that the elliptical excitation beam 1316 impinges on the microfluidic device 100 at a non-normal angle of incidence $\varphi$. In a preferred embodiment, $\varphi$ is approximately 45° relative to the plane defined by microfluidic device 100, although other non-normal angles of incidence may be used, e.g., from about 30° to about 100°. In one embodiment, source 1310 and optical elements 1314 are arranged such that the elliptical excitation beam 1316 is polarized with a polarization direction/vector 1318 that is substantially parallel to the major axis of the elliptical excitation beam 1316.

The optical elements 1314 are also preferably arranged such that the major axis of the resulting elliptical excitation beam 1316 is substantially perpendicular to the direction of the micro-channels 1322 in the detection region 1325 as shown. Alternatively, the major axis of the elliptical excitation beam spot 1316 is oriented along the length of one or more of the microchannels 1322 in the detection region 1325. This orientation excites and detects a longer region of each of the microchannels 1322, e.g., where a time dependent reaction is being monitored, or where detection sensitivity requires extended detection. In this manner, substances (not shown) in each of the microfluidic channels 1322 may be simultaneously excited by the elliptical excitation beam 1316.

Emissions emanating from the samples 109 in each of the plurality of the microchannels 1322 in the detection region 1325 are focused and/or directed by one or more optical elements 1334 (two elements shown) onto the detector array 1320. At least one optical element, e.g., element 1334', such as an objective lens, is preferably positioned to direct emissions received from the detection region 1325 in a direction normal to the plane defined by the microfluidic device 100 as shown. One or more band-pass filter elements 1336 are provided to help prevent undesired wavelengths from reaching detector array 1320. The detector results then are processed over time to monitor the reaction. The light source may also be a light emitting diode ("LED"), which would typically have a larger illumination spot size. When detecting the reaction product in a dual rotor system, one or both rotors will move out of the optical path.

Although not shown, the radiation 1316 strikes the PCR reaction reservoirs 138, shown best in FIG. 1D, through the cutout 170 in the cover 160 in the illustrated embodiment. As was mentioned above, the cover 160 may be omitted, or the cover 160 may be employed and the cutout 170 omitted. Where the cutout 170 is omitted, the material from which the cover 160 is fabricated from a material optically transmissive at the wavelengths employed by the particular fluorescent monitoring techniques. The cutout 170 may also be omitted from the cover 160 in embodiments in which fluorescent monitoring is not performed.

As another example of a variation found in some embodiments, not all PCR protocols employ three thermal cycles. Some only employ two thermal cycles. In these PCR protocols, one cycles only between the denaturation and annealing temp and no dwell time is spent at those temperatures. The idea is that in an optimized assay, just reaching 95° C. is sufficient for denaturation and just touching the annealing temp, say 60° C., is enough for annealing. No time is spent at the extension step because the enzyme is active during the ramp from 60° C. to 95C. Even though no time is spent at the optimum temp for activity of 72° C.-74° C., there is enough activity during the ramp to yield a PCR. Thus, as few as two thermal elements may be used to implement certain PCR protocols.

Another alternative protocol calls for what is known as "thermal ramping." One or more times while thermally cycling the microfluidic sample 109, or after completing thermal cycling, one of the heating elements can be ramped while thermally connected to the microfluidic sample 109. Thermal ramping is typically combined with fluorescent monitoring, which was discussed above and performed at the same time.

Figure 14A:
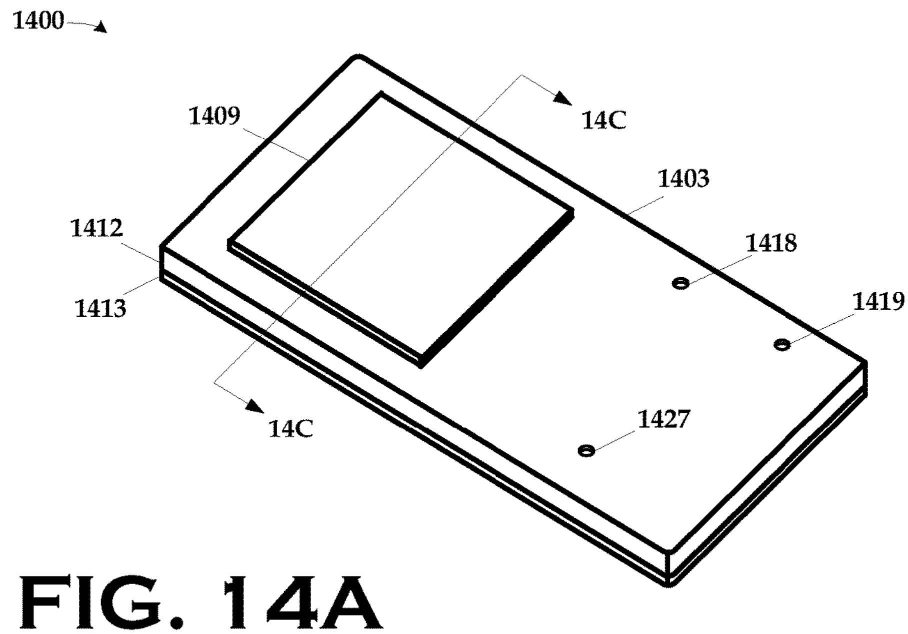
FIG. 14A-FIG. 14C depict a microfluidic device in accordance with the present invention in a second embodiment.
Figure 14B:
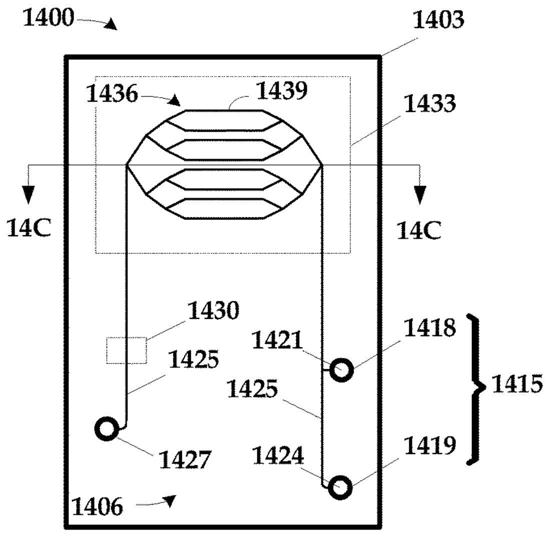
Figure 14C:
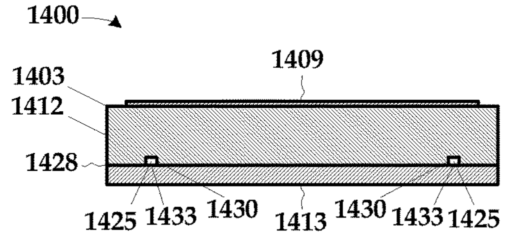
Figure 15A:
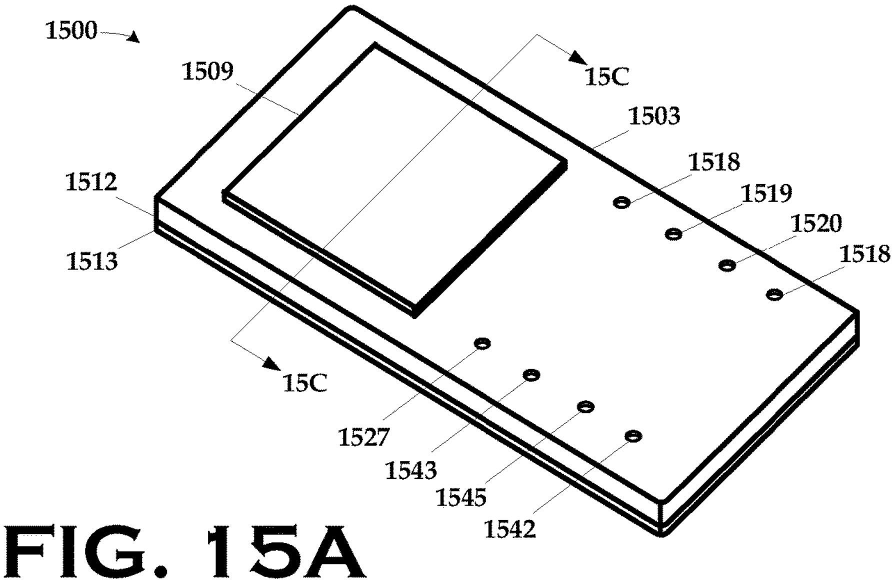
FIG. 15A-FIG. 15D depict a microfluidic device in accordance with the present invention in a third embodiment.
Figure 15B:
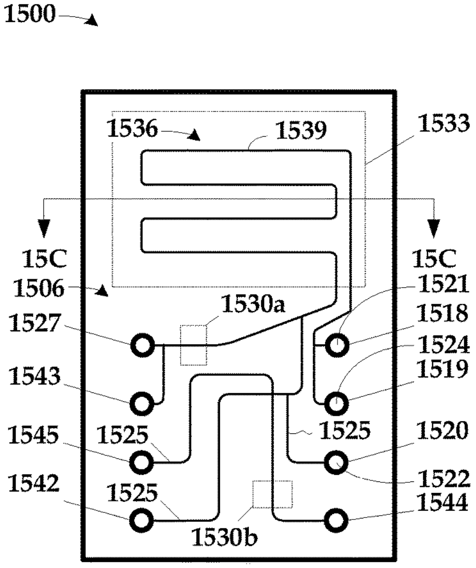
Figure 15C:
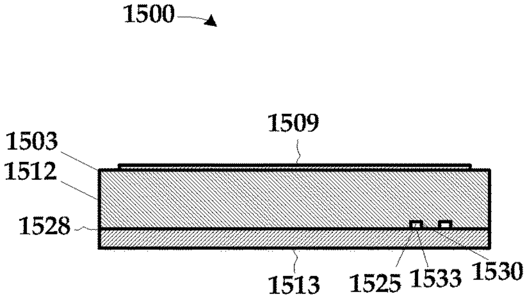
Figure 16:
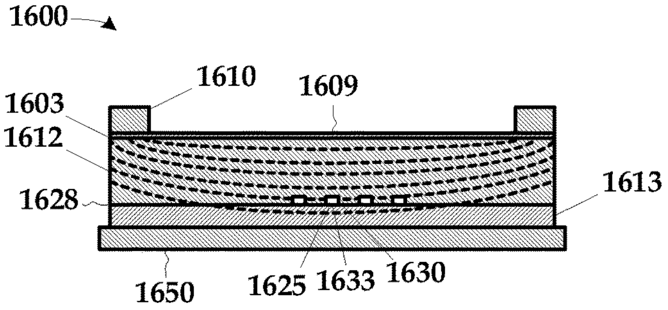
FIG. 16 depicts a microfluidic device in accordance with the present invention in a fourth embodiment.

As was mentioned above, the invention admits wide variation in the implementation of the microfluidic device of the present invention. FIG. 14A-FIG. 16 illustrate three further alternative embodiments of the microfluidic device. More particularly:

FIG. 14A-FIG. 14C depict a microfluidic device in accordance with the present invention in a second embodiment;

FIG. 15A-FIG. 15C depict a microfluidic device in accordance with the present invention in a third embodiment; and FIG. 16 depicts a microfluidic device in accordance with the present invention in a fourth embodiment.

Each of these embodiments will now be discussed in turn.

FIG. 14A and FIG. 14C are a perspective view, a top, plan view, and a cross-sectional view, respectively, of a body structure 1400 for use in a microfluidic device. Note that the caddy has been omitted. The cross-sectional view of FIG. 14C is taken along line 14C-14C shown in both FIG. 14A and FIG. 14B. In general, the body structure 1400 comprises a plate 1403, a microfluidic PCR circuit 1406 (best shown in FIG. 14B) and a heating element 1409 (best shown in FIG. 14A). Note that the heating element 1409 is omitted from FIG. 14B to promote clarity in the disclosure of the microfluidic PCR circuit 1406.

The plate 1403 is fabricated, in the illustrated embodiment, from a plastic, such as COC. The plate 1403 comprises a first, or "top", layer 1412 and a second, or "bottom" layer 1413. Note that the terms "top" and "bottom" are defined relative to their nominal orientations when the PCR device of the body structure 1400 is in use. In the illustrated embodiment, the first layer 1412 is approximately three times as thick as the first layer 1413—e.g., 300 μm to 100 μm thick. (The heating element 1609 is fabricated approximately 10 nm thick.) The term "approximately" is an accommodation to certain factors such as manufacturing tolerances, etc., the may interfere with some embodiments being able to achieve high degrees of precision. However, the relative thicknesses of the first and second layers 1412, 1413 is not material to the practice of the invention in this embodiment so long as the resultant device performs as intended by the invention.

The microfluidic PCR circuit 1406 generally includes a plurality 1415 of ports 1418, 1419 formed in the plate 1403 into which the PCR components may be loaded, e.g., the enzyme 1421 and the DNA and deoxyNucleotideTriPhosphate ("dNTP") 1424. The microfluidic PCR circuit 1406 also includes a port 1427 formed in the plate 1403 by which an electrokinetic force may be imparted to the loaded PCR components 1421, 1424. The body structure 1400 imparts the electrokinetic force through, in the illustrated embodiment, a continuous flow vacuum. A plurality of microfluidic channels 1425, shown best in FIG. 14B, interconnect the ports 1418, 1419, 1427 to define the microfluidic PCR circuit 1406.

More particularly, with respect to the microfluidic channels 1425, note that the microfluidic channels 1425 are actually fabricated in the interior of the body structure 1400. More particularly, as is best shown in FIG. 14B, the microfluidic channels 1425 are formed at the interface 1428 between the first and second layers 1412, 1413. The first layer 1412 defines an upper portion 1430 for each of the ports 1418, 1419, 1427 and the microfluidic channels 1425. The second layer 1413 defines the terminus (not shown) for each of the 1418, 1419, 1427 ports and a lower portion, or floor, 1433 of the microfluidic channels 1425. However, this is not necessary to the practice of the invention.

The microfluidic PCR circuit 1406 also includes a detection window 1430. This particular embodiment is intended for use with a fluorescent monitoring technique such as that disclosed above relative to FIG. 13A-FIG. 13B. Optical detection windows are typically transparent such that they are capable of transmitting an optical signal from the channel/chamber over which they are disposed. The detection window 1430 is a solid area of the plate 1403 that is non-optically active, or optically transmissive, in the frequency range employed in the monitoring technique. That is, the optical detection window may merely be a region of a transparent layer 1412 where the first layer 1412 is constructed of an optically transparent polymer material, e.g., PMMA, polycarbonate, etc. Thus, the detection window 1430 is not an opening, port, or aperture in the plate 103 in this particular embodiment, although it may be in other embodiments. Alternatively, where opaque substrates are used in manufacturing the devices, transparent detection windows fabricated from the above materials may be separately manufactured into the device.

Note that this characteristic of the detection window 1430 impacts material selection at least for that part of the plate 1403. There is no requirement that the entire plate 1403 be fabricated from the same material. However, it will generally be convenient to fabricate at least each of the first and second layers 1412, 1412 from the same material throughout. Thus, the first layer 1412 will typically, in this particular embodiment, be fabricated of a material that is optically transmissive in the frequency range employed in the monitoring technique.

The footprint 1433 of the heating element 1409 is shown in FIG. 14B in which the microfluidic PCR circuit 1406 is best shown. That portion of the microfluidic PCR circuit 1406 lying under the footprint 1433 is to be heated by the heating element 1409. It is also that portion in which the PCR reaction occurs in this particular embodiment. Note that this portion of the microfluidic PCR circuit 1406 comprises a plurality 1436 of parallel, branching channels 1439 (only one indicated). This structure helps facilitate the PCR reaction in this particular embodiment by providing a larger flow volume at the point at which heating occurs.

The heating element 1409 is formed on the plate 1403 and permits a portion of the microfluidic PCR circuit 1406 to be selectively heated. More particularly, in this embodiment, the heating element 1409 heats that portion of the microfluidic PCR circuit 1406 comprising the plurality 1436 of parallel, branching channels 1439. The heating element 1409 will typically employ a resistive heating. To this end, a voltage can be applied across the heating element 1409 to generate a current therethrough, which will generate heat therein that will conduct into the plate 1403. The heating element 1409 can be formed on the plate 1403 using any suitable technique known to the art. In the illustrated embodiment, the heating element 1409 is formed on the plate 1403 using a physical vapor deposition techniques such as is port known to those in the art. However, the heating element 1409 may alternatively be separately fabricating and adhered or fastened to the plate 1403. Any suitable technique known to the art may be used.

In operation, the enzyme 1421 and the DNA and dNTP 1424 are loaded into the ports 1418, 1419, respectively. A continuous flow vacuum is applied through the port 1427 to impart the electrokinetic force to the enzyme 1421 and the DNA and dNTP 1424. The heating element 1409 is heated to the proper temperature so that, when the enzyme 1421 and the DNA and dNTP 1424 mixture enters the plurality 1436 of parallel, branching channels 1439, it can begin the thermal cycling for the PCR reaction. Note that the level of the vacuum is selected so that the mixture remains in the reaction chamber while the PCR reaction occurs. When the PCR reaction is completed, the vacuum is applied once again and the result monitored through the detection window. Detection can be performed by either using continuous flow or just filling the microfluidic channels 1425 and monitoring for clouds of fluorescence. Note that quantitation is possible in this particular embodiment, as port.

FIG. 15A and FIG. 15C are a perspective view, a top, plan view, and a cross-sectional view, respectively, of a body structure 1500. Note that the caddy has been omitted. The cross-sectional view of FIG. 15C is taken along line 15C-15C shown in both FIG. 15A and FIG. 15B. In general, the body structure 1500 comprises a plate 1503, a microfluidic PCR circuit 1506 (best shown in FIG. 15B) and a heating element 1509 (best shown in FIG. 15A). Note that the heating element 1509 is omitted from FIG. 15B to promote clarity in the disclosure of the microfluidic PCR circuit 1506.

The plate 1503 is fabricated in largely the same manner as is the plate 1403 in FIG. 14A-FIG. 14C, using the same types of techniques and materials. Thus, the plate 1503 comprises a first, or "top", layer 1512 and a second, or "bottom" layer 1513 constructed from a plastic such as COC and the first layer 1512 is approximately three times as thick as the first layer 1513—e.g., 300 μm to 100 μm thick. The microfluidic channels 1525 are fabricated in the interior of the body structure 1500 and, as is best shown in FIG. 15B, are formed at the interface 1528 between the first and second layers 1512, 1513. The first layer 1512 defines an upper portion 1530 (only one indicated) for each of the ports 1518, 1519, 1527 and the microfluidic channels 1525. The second layer 1513 defines the terminus (not shown) for each of the 1518, 1519, 1527 ports and a lower portion, or floor, 1533 (only one indicated) of the microfluidic channels 1525. The detection windows 1530*a*, 1530*b* are solid areas of the plate 1503 that are optically transmissive in the frequency range employed in the monitoring technique.

The heating element 1509 is also fabricated and employed similarly to the heating element 1409 in FIG. 14A-FIG. 14C. The heating element 1509 is formed on the plate 1503 and permits a portion of the microfluidic PCR circuit 1506 to be selectively heated. The heating element 1509 will typically employ a resistive heating, e.g., by application of a voltage applied across the heating element 1509 to generate a current therethrough. The heating element 1509 can be formed on the plate 1503 using any suitable technique known to the art and, in this particular embodiment, using a physical vapor deposition technique such as is port known to those in the art.

However, the microfluidic PCR circuit 1506 of the embodiment in FIG. 15A-FIG. 15C differs from the microfluidic PCR circuit 1406 in FIG. 14A-FIG. 14C. As is apparent from the above discussion, for example, it employs two detection windows 1530*a*, 1530*b*, one for detecting without separation and one for detecting with separation, respectively. Also, that portion of the microfluidic PCR circuit 1506 lying under the footprint 1533 comprises a plurality 1536 of looping, continuous channels 1539 (only one indicated) to be heated by the heating element and in which the PCR reaction occurs.

The microfluidic PCR circuit 1506 also differs in the number of ports it employs. In addition to the loading ports 1518, 1519 for the enzyme 1521 and the DNA and dNTP 1524, but also a loading port 1530 for a DNA ladder reference 1522 such as is commonly used in the art. In addition to the port 1527 through which a continuous flow vacuum may be applied, the microfluidic PCR circuit 1506 also includes ports 1542, 1543 by which positive and negative load voltages, respectively, may be applied and ports 1544, 1545 by which positive and negative separation voltages may be applied, respectively.

The microfluidic PCR circuit 1506 also differs in the number of ports it employs. In addition to the loading ports 1518, 1519 for the enzyme 1521 and the DNA and dNTP 1524, but also a loading port 1530 for a DNA ladder reference 1522 such as is commonly used in the art. In addition to the port 1527 through which a continuous flow vacuum may be applied, the microfluidic PCR circuit 1506 also includes ports 1542, 1543 by which positive and negative load voltages, respectively, may be applied and ports 1544, 1545 by which positive and negative separation voltages may be applied, respectively.

Figure 15D:
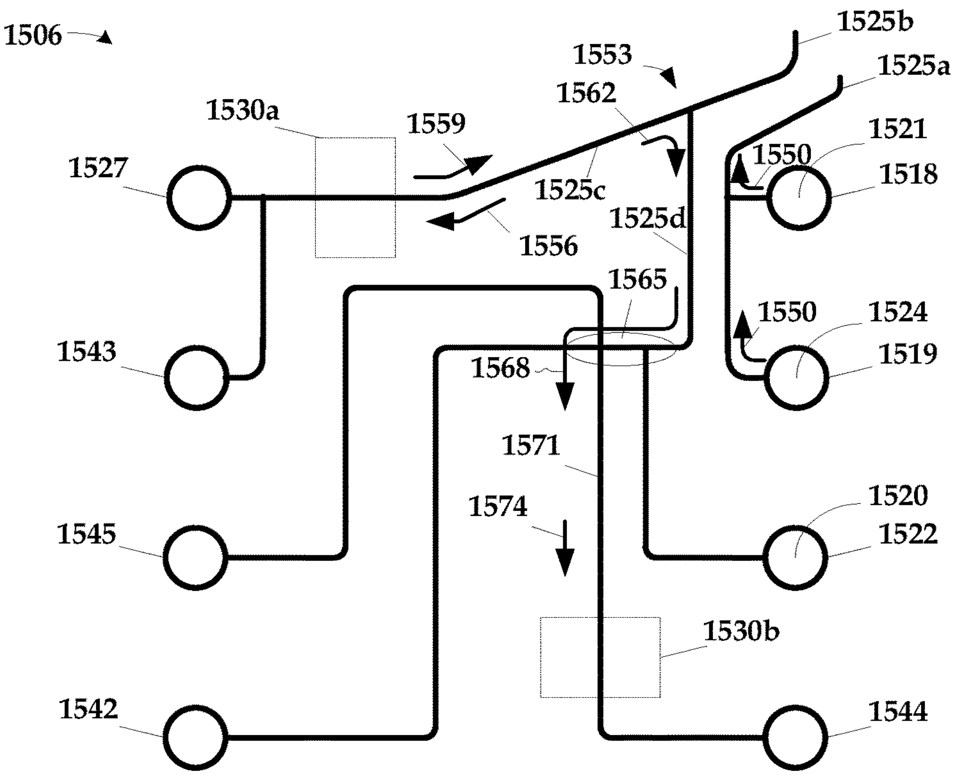

Turning now to FIG. 15D, in operation, the enzyme 1521, the DNA and dNTP 1524, and the DNA ladder 1522 are loaded into the ports 1518-1520, respectively. A continuous vacuum is applied through the port 1527, which pulls the components out of the ports 1518-1520 and to the looping, continuous channels 1539 (shown in FIG. 15B) as indicated by the arrows 1550. As the components pass through the channel 1525*a*, they mix to create the reaction solution before entering the channels 1539 in which the PCR reaction takes place. The length of the channels 1539 and the level of the vacuum imparted via the port 1527 are designed so that the mixture of the enzyme 1521 and the DNA and dNTP 1524 remains in the channels 1539 for the duration of the PCR protocol for the desired number of thermocycles. As the mixture passes through the channels 1529, the heating element 1509 and, in some embodiments, an external thermal element (not shown) thermocycle the mixture at the temperatures and for the durations specified by the PCR protocol being applied.

Once the PCR reaction is complete, a load voltage is imposed on the microfluidic circuit 1506 via the ports 1543, 1542 to impart an electrokinetic force to the mixture. More particularly, a negative load voltage is applied to the port 1543 and a positive load voltage is applied to the port 1542. This imparts an electro-osmotic force such that the mixture travels from the channels 1539 through the channel 1525*b* and the intersection 1553 to the detection window 1530*a* on the channel 1525*c* as indicated by the arrow 1556. (The channels 1525*b*-1525*c* are coated in a manner known to the art to help facilitate the electro-osmotic movement.) At this point, fluorescent monitoring can yield detection without separation.

Once the mixture reaches the detection window 1530*a*, the load voltages are lifted from the ports 1543, 1542 and a separation voltage is imposed on the ports 1545, 1544. More particularly, a positive negative separation voltage is imposed on the port 1545 and a positive separation voltage on the port 1544. (Note that the timing can be determined from the flow rate of the mixture.) This imparts an electrophoretic force on the mixture, causing it to reverser course in the channel 1525*c* back toward the intersection 1553, as represented by the arrow 1559.

At the intersection 1553, the electrophoretic force turns the mixture into the channel 1525*d*, as indicated by the arrow 1562, and approaches the intersection 1565. (The channel 1525*d* is coated in a manner known to the art to help inhibit electro-osmotic movement.) The electrophoretic force turns the mixture into the channel 1525*e* at the intersection 1565, as indicated by the arrow 1571. The electrophoretic force continues driving the mixture, as indicated by the arrow 1574, to the detection window 1530*b*. At this point, fluorescent monitoring will yield detection with separation.

FIG. 16 is a cross-sectional view of a body structure 1600 in a fourth embodiment of the present invention. Note that the caddy has been omitted once again. In general, the body structure 1600 comprises a plate 1603, a microfluidic PCR circuit (shown only by the channels 1625) and a heating element 1609. Note that the heating element 1609 includes two contacts 1610 by which the voltage may be applied. Note also that FIG. 16 also shows a thermal element 1650, which may be a thermal element from a thermocycler such as those disclosed above. Alternatively, the thermal element 1650 may be a Peltier device, such as are known in the art for use in temperature control.

The plate 1603 is fabricated in largely the same manner as is the plate 1403 in FIG. 14A-FIG. 14C, using the same types of techniques and materials. Thus, the plate 1603 comprises a first, or "top", layer 1612 and a second, or "bottom" layer 1613 constructed from a plastic such as COC, and the first layer 1612 is approximately three times as thick as the first layer 1613—e.g., 300 μm to 100 μm thick. The microfluidic channels 1625 are fabricated in the interior of the body structure 1600 and, as is best shown in FIG. 16B, are formed at the interface 1628 between the first and second layers 1612, 1613. Thus, unlike in conventional practice where microfluidic channels typically are fabricated in the middle of the body structure, the microfluidic channels 1625 are fabricated toward the bottom of the body structure 1600. The first layer 1612 defines an upper portion 1630 (only one indicated) for each of the ports (not shown) and the microfluidic channels 1625. The second layer 1613 defines the terminus (not shown) for each of the ports and a lower portion, or floor, 1633 (only one indicated) of the microfluidic channels 1625. Although not shown, the body structure 1600 also includes detection windows as described for the alternative embodiments disclosed above.

The heating element 1609 is also fabricated and employed similarly to the heating element 1409 in FIG. 14A-FIG. 14C. The heating element 1609 is formed on the plate 1603 and permits a portion of the microfluidic PCR circuit 1606 to be selectively heated. The heating element 1609 will typically employ a resistive heating, e.g., by application of a voltage applied across the heating element 1609 at the contacts 1610 to generate a current. The heating element 1609 can be formed on the plate 1603 using any suitable technique known to the art, such as physical vapor deposition.

The heating element 1609 and the thermal element 1650 establish a temperature gradient through the first layer 1612. Isothermal lines 1652 (only one indicated), shown in broken lines, illustrate the conduction of heat generated by the heating element 1609 through the first layer 1612 in the presence of the temperature gradient. The material of the first layer 1612 and the temperature gradient dampen the conduction to produce the profile presented. Note that the isothermal lines 1652 are nearly flat at the microfluidic channels 1625, which is desirable so that the microfluidic channels 1652 can heat uniformly. This is one desirable consequence of fabricating the microfluidic channels 1625 toward the bottom of the body structure 1600. Note that, even in the presence of completely flat isothermal lines 1652, the microfluidic channels 1625 will experience 4 C temperature variations within due to Taylor-Ari-like behavior. These heating principles apply equally to those embodiments disclosed in FIG. 14A-FIG. 14C and FIG. 15A-FIG. 15C.

Note that the various aspects of the disclosed embodiment are but various means by which the associated functionalities may be implemented. For instance, in each of the embodiments shown in FIG. 14A-FIG. 14C and FIG. 15A-FIG. 15C, the microfluidic channels therein are but two different means for interconnecting the ports of the microfluidic PCR circuit. Other means may instead comprise channels formed in the bottom layer, for instance. Also:

- other embodiments may vary the layout of the microfluidic channels that are selectively heated by the heating elements;
- alternative embodiments may also employ means for detecting the fluorescence emanating from the microfluidic PCR circuit other than the disclosed detection windows, where fluorescent monitoring is employed;
- alternative embodiments may alternatives to the ports shown for loading PCR components and for imparting the electrokinetic force; and
- means for selectively heating a portion of the microfluidic PCR circuit.

Still other alternative embodiments may employ other, alternative means.

Thus, that aspect of the invention presented in FIG. 14A-FIG. 16 presents a number of advantages relative to conventional practice. For instance, in some embodiments, it presents a disposable chip platform for research and/or diagnostics that can be located near the sample source and preparation can be manual or automated. It is furthermore compatible with a wide array of assays and tests such as gene expression, multiplexed assays, low sample concentration (if throughput is not important) and isothermal amplification. Note, however, that not all embodiments will necessarily exhibit all such advantages and that those in the art may appreciate other advantages not set forth.

This concludes the detailed description. The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An apparatus for use with a microfluidic device, the apparatus comprising:

- a plurality of thermal elements, each of the plurality of thermal elements being temperature controlled;
- a thermal element tray operable to mount the plurality of thermal elements, the plurality of thermal elements being mounted parallel to each other;
- a drive operable to move the microfluidic device laterally relative to the thermal element tray and align one of the plurality of thermal elements with a heating area of the microfluidic device; and
- a lift operable to move the aligned one of the plurality of thermal elements tangentially relative to the microfluidic device to contact the heating area.

2. The apparatus of claim 1, wherein the thermal elements comprise a plurality of bars.

3. The apparatus of claim 2, wherein the drive is operably connected to control the lift.

4. The apparatus of claim 1, wherein the lift includes:

a rotatable shaft; and a plurality of bars radially mounted about the rotatable shaft;

wherein the lift is further operable to move one of the plurality of bars to contact the aligned one of the plurality of thermal elements.

5. The apparatus of claim 1, wherein the lift includes a linear actuator operable to move the aligned one of the plurality of thermal elements.

6. The apparatus of claim 1, further comprising a processor responsive to a protocol application to control positions of and temperatures of each of the plurality of thermal elements.

7. The apparatus of claim 1, wherein each of the plurality of thermal elements is selected from the group consisting of a resistive element and a Peltier device.

8. The apparatus of claim 1, wherein at least one of the drive and the lift is operable to position one of the plurality of thermal elements and the microfluidic device such that the one of the plurality of thermal elements contacts the top of the microfluidic device.

9. The apparatus of claim 1, wherein at least one of the drive and the lift is operable to position one of the plurality of thermal elements and the microfluidic device such that the one of the plurality of thermal elements contacts the bottom of the microfluidic device.

10. The apparatus of claim 1, wherein at least one of the drive and the lift is operable to position one of the plurality of thermal elements above the microfluidic device and the microfluidic device such that the one of the plurality of thermal elements above the microfluidic device contacts the top and the bottom of the microfluidic device, and to position one of the plurality of thermal elements below the microfluidic device and the microfluidic device such that the one of the plurality of thermal elements below the microfluidic device contacts the bottom of the microfluidic device.

11. The apparatus of claim 6, wherein the processor is further responsive to the protocol application to thermally ramp at least one of the plurality of thermal elements when the at least one of the plurality of thermal elements contacts the heating area.

12. The apparatus of claim 6, wherein the processor is further responsive to the protocol application to break contact between at least one of the plurality of thermal elements and the heating area.

13. The apparatus of claim 12, wherein the processor is further responsive to the protocol application to thermally ramp at least one of the plurality of thermal elements during the respective period of time the at least one of the plurality of thermal elements contacts the microfluidic device.

14. The apparatus of claim 1, further comprising an interface material imposed between the aligned one of the plurality of thermal elements and the heating area when the aligned one of the plurality of thermal elements contacts the heating area.

15. The apparatus of claim 14, wherein the interface material is selected from the group consisting of a wax, a polymer, and a thermally conductive insulator material.

16. The apparatus of claim 6 wherein the processor is further responsive to the protocol application to successively contact each of the plurality of thermal elements with the heating area and to control temperature for one of the plurality of thermal elements in contact with the heating area to bring temperature of the heating area to a predetermined temperature for a predetermined time.

* * * * *